United States Patent
Hao et al.

(10) Patent No.: US 10,195,208 B2
(45) Date of Patent: Feb. 5, 2019

(54) COMBINATION THERAPY

(71) Applicant: Novartis AG, Basel (CH)

(72) Inventors: Huaixiang Hao, Malden, MA (US); Xizhong Huang, Southborough, MA (US); Angela Tam, Randolph, MA (US); Shailaja Kasibhatla, San Diego, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/328,710

(22) PCT Filed: Jul. 29, 2015

(86) PCT No.: PCT/IB2015/055737
§ 371 (c)(1),
(2) Date: Jan. 24, 2017

(87) PCT Pub. No.: WO2016/016822
PCT Pub. Date: Feb. 4, 2016

(65) Prior Publication Data
US 2017/0209457 A1    Jul. 27, 2017

Related U.S. Application Data

(60) Provisional application No. 62/031,583, filed on Jul. 31, 2014.

(51) Int. Cl.
| | | |
|---|---|---|
| *A61K 31/55* | (2006.01) | |
| *A61K 31/53* | (2006.01) | |
| *C07D 401/14* | (2006.01) | |
| *C07D 487/04* | (2006.01) | |

(52) U.S. Cl.
CPC .............. *A61K 31/55* (2013.01); *A61K 31/53* (2013.01); *C07D 401/14* (2013.01); *C07D 487/04* (2013.01)

(58) Field of Classification Search
CPC ...... A61K 31/55; A61K 31/53; C07D 487/04; C07D 401/14
See application file for complete search history.

(56) References Cited

FOREIGN PATENT DOCUMENTS

| | | |
|---|---|---|
| KR | 101418970 B1 | 7/2014 |
| WO | 2013/149581 A1 | 10/2013 |
| WO | 2013/184757 A1 | 12/2013 |
| WO | WO-2013184757 A1 * | 12/2013 ......... A61K 31/4184 |

OTHER PUBLICATIONS

Liu, X., "A novel kinase inhibitor INCB28060 blocks c-MET-dependent signaling, neoplastic activities, and crosstalk with EGFR and HER-3." Clinical Cancer Research (2011): clincanres:7127-7138.*

* cited by examiner

*Primary Examiner* — John M Mauro
(74) *Attorney, Agent, or Firm* — David K. Cheung

(57) ABSTRACT

The present disclosure relates to pharmaceutical products comprising a combination of (i) a MET inhibitor which is INC280 or a pharmaceutically acceptable salt or hydrate thereof and (ii) an EGFR inhibitor described herein, which are jointly active in the treatment of proliferative diseases, corresponding pharmaceutical formulations, uses, methods, processes, commercial packages and related embodiments.

26 Claims, 12 Drawing Sheets

Figure 1 C-Met/EGFR combo with INC280/Compound A in HCC827 and HCC-827 GR

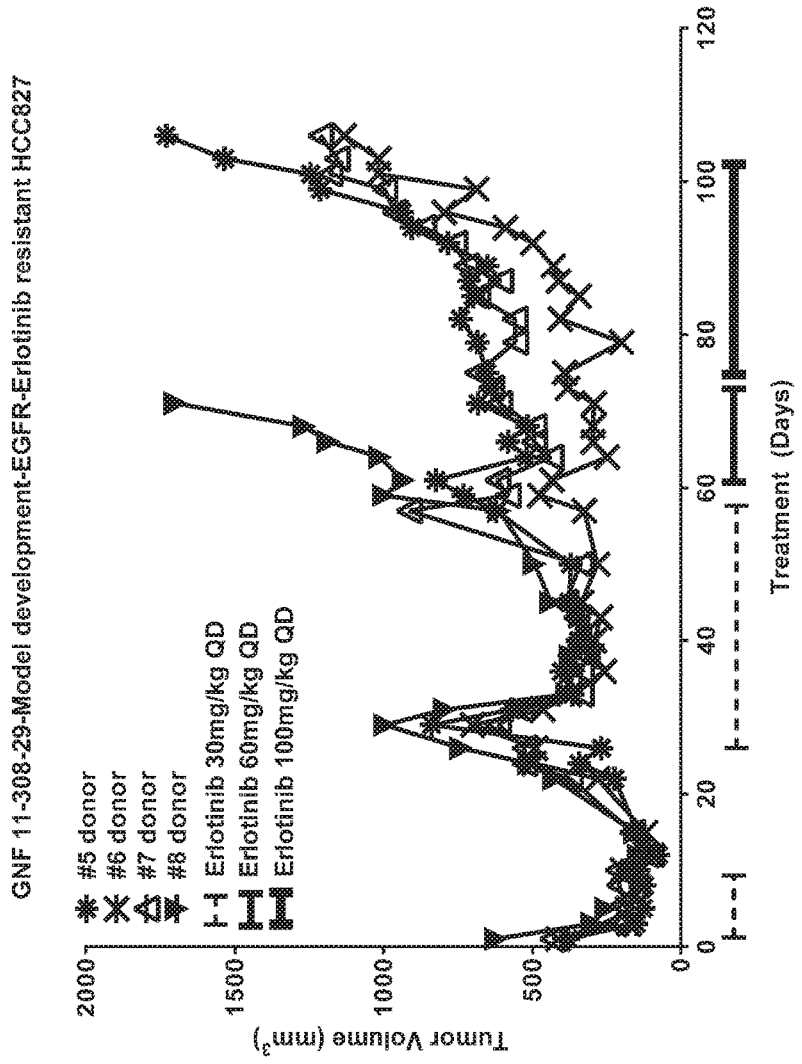
Figure 5 Donor study and confirmation of Erlotinib resistant NCI-HCC827 xenograft model Figure 6. Confirmation of phospho MET activity by pRTK analysis (study 11-308-29 donor source for 11-308-138)
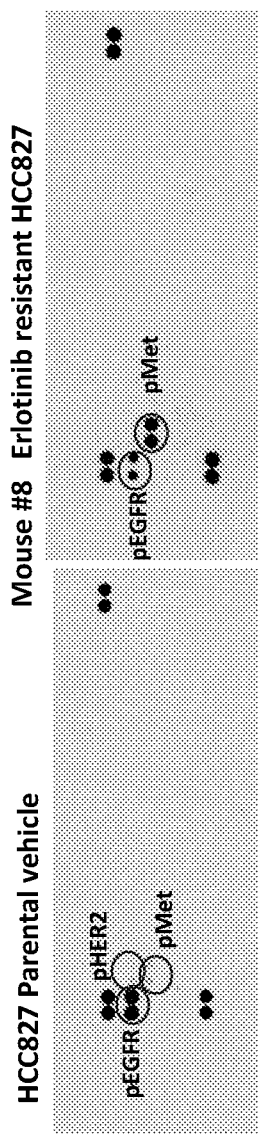
Phospho RTK array shows tumor lysates from HCC827 parental and animal 8.

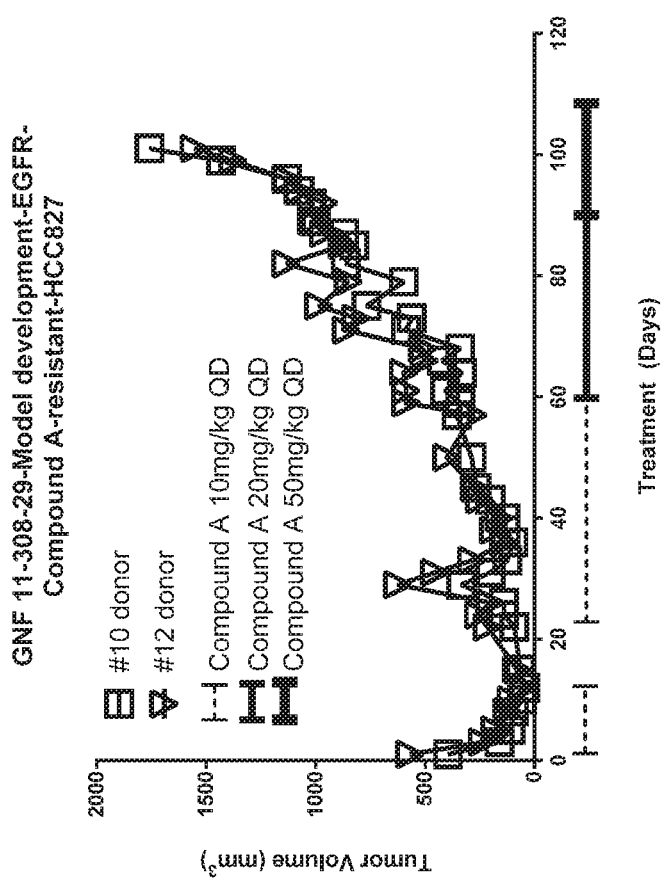
Figure 7 Donor study and confirmation of Compound A resistant NCI-HCC827 xenograft model Figure 8 Confirmation of phospho MET activity by pRTK analysis (study 11-308-29 donor source for 11-308-138)
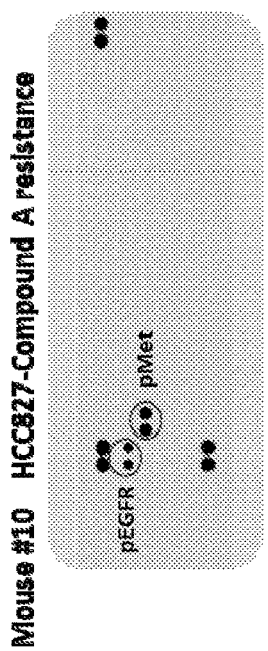
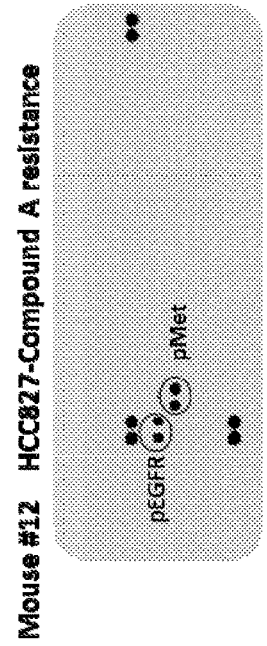
The RTK blot in Figure 8 shows tumor lysates from study 11-308-29 animals 10, 12 (11-308-29 Animal #10 donor source for 11-308-138)

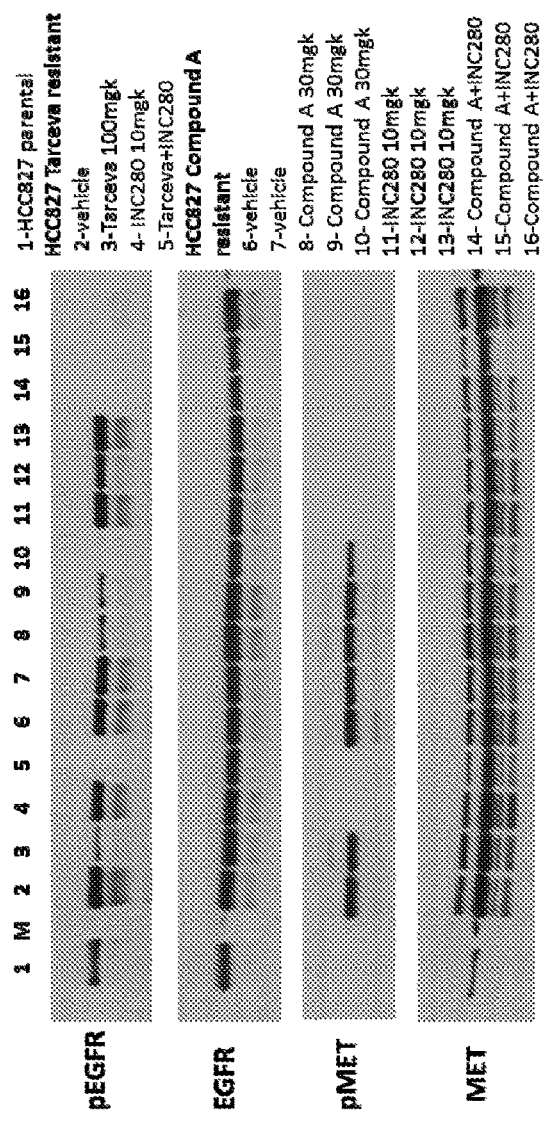
Figure 9 PD western using tumor lysates shows selective depletion of pEGFR and pMET expression using Compound A and or INC280.

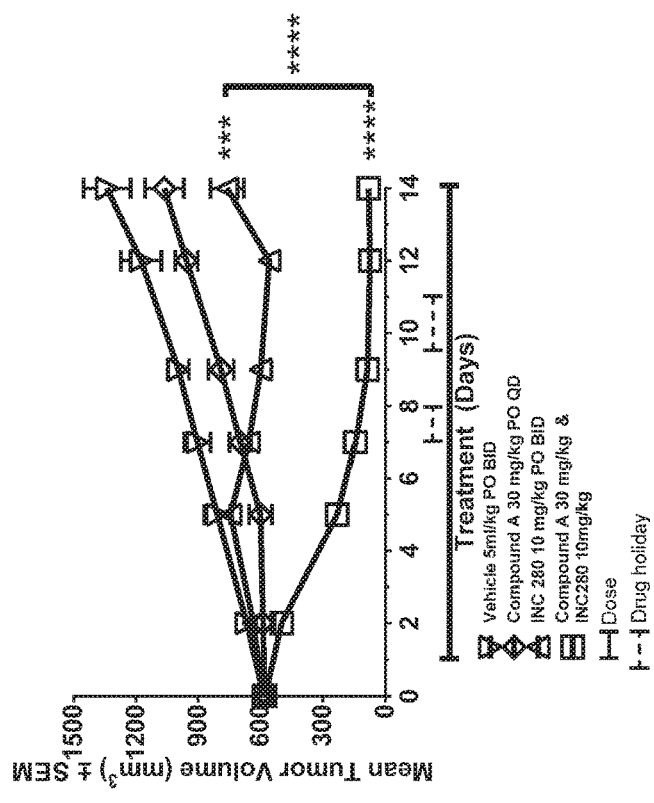
Figure 10 *In vivo* efficacy of compound A in combination with INC280 in an compound A resistant NCI-HCC827 mouse xenograft model
Treatment of vehicle, Compound A and INC280 started on day 0 (23 days post tumor transplantation). Significant differences were calculated using One-Way ANOVA post hoc Tukey multiple comparison test on day 14 with N=6 per group, (*p<0.001, ** p<0.0001).

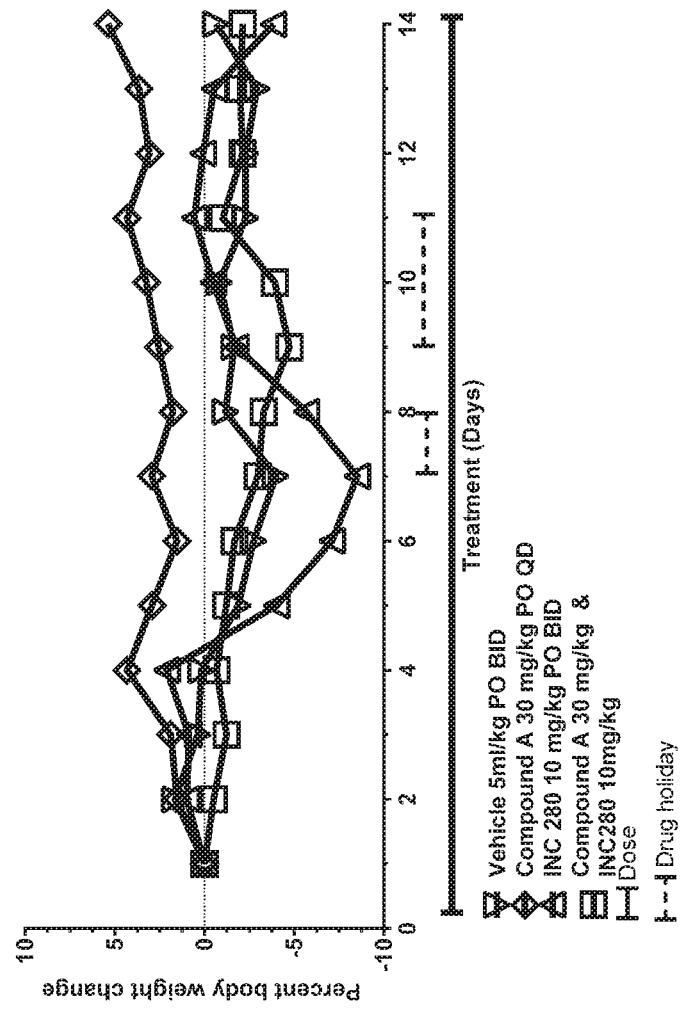
Figure 11 Percent body weight change in in the combination study

Figure 12 IHC and Histology
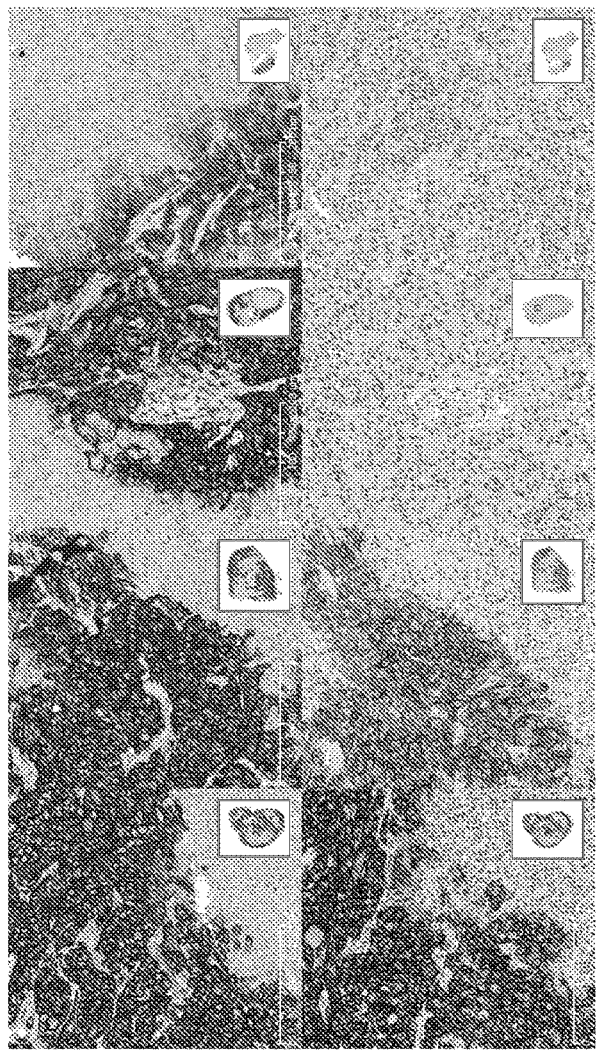
Top panel is pEGFR IHC (p-EGFR(D),MS,HU'; Histology Immunohistochemistry SOP 33) 100x Bottom panel is pMET IHC (p-Met (D),HU; Histology Immunohistochemistry SOP 53) 100x. From left to right, vehicle, Compound A, INC280, combination Compound A/INC280

COMBINATION THERAPY

FIELD OF THE DISCLOSURE

The present disclosure relates to pharmaceutical combinations, e.g. products, comprising a combination of (i) a MET inhibitor or a pharmaceutically acceptable salt or hydrate thereof and (ii) an EGFR (ErbB-1) inhibitor, which are jointly active in the treatment of proliferative diseases, corresponding pharmaceutical formulations, uses, methods, processes, commercial packages and related embodiments.

BACKGROUND OF THE DISCLOSURE

Drugs that were designed to act against individual molecular targets often are not appropriate to combat diseases with more than one target as cause (multigenic diseases), such as cancer or other proliferative diseases.

In order to combat such diseases, one approach is to use single multi-target drugs—however, here it is required that the targets causally involved into manifestation of a disease are all hit by the drug considered. On the other hand, multi-target drugs may lead to undesired side effects as they may also have impact on targets not involved in the disease manifestation.

A different approach is to use a combination of drugs as multi-target drugs. In the best scenario, this may lead to a combined efficiency, e.g. synergy, thus even allowing a reduction of side effects caused by the single drugs when used alone.

Occasionally, the components (combination partners) of such drugs may impact separate targets to create a combination effect, and thus may create a combination effect going beyond what is achievable with the single compounds and/or when considering their isolated effects, respectively, either in the same pathway or separate pathways, within an individual cell or in separate cells in separate tissues. Alternatively, one component may alter the ability of another to reach its target, e.g. by inhibiting of efflux pumps or the like. Yet alternatively, the combination partners may bind to separate sites of the same target. These variants of target connectivity hamper the search for appropriate combinations by hugely increasing the possible types of interactions that might be useful for combination or not.

However, a desired cooperation, or even a synergy, using such drugs may not be found in many cases. As the number of pairwise (r=2) drug combinations increases according to the formula n!/(r!(n-r)!) with the number of agents n being tested (e.g. testing 2000 agents would already generate 1,999,000 unique pairwise combinations), an appropriate screening method allowing high efficiency is necessary.

In addition, before any combination is considered, there is a crucial requirement to identify the pathways, enzymes, metabolic states or the like that are involved causally or in a supporting way in the disease manifestation.

In many cases, it is not even known at all that a given disease is multigenic.

Therefore, the search for appropriate combinations and amounts can properly be described to correspond to finding a needle in a haystack.

The proto-oncogen cMET (MET) encodes the protein Hepatocyte Growth Factor Receptor (HGFR) which has tyrosine kinase activity and is essential for embryonic development and wound healing. Upon Hepatocyte Growth Factor (HGF) stimulation, MET induces several biological responses, leading to invasive growth. Abnormal MET activation triggers tumor growth, formation of new blood vessels (angiogenesis) and metastasis, in various types of malignancies, including cancers of the kidney, liver, stomach, breast and brain. A number of MET kinase inhibitors are known, and alternatively inhibitors of HGF-induced MET (=HGFR) activation. The biological functions of c-MET (or c-MET signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

A dysregulated c-Met (c-MET) pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1):1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. In addition to the abnormal HGF/c-Met expression, c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement.

The various cancers in which c-MET is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-MET pathway contributes to tumor formation and progression and could be a good target for effective cancer intervention has been further solidified by numerous preclinical studies (Birchmeier, C. et al., Nat. Rev. Mol. Cell Biol. 2003, 4(12):915-925; Christensen, J. G. et al., Cancer Lett. 2005, 225(1):1-26; Corso, S. et al., Trends in Mol. Med. 2005, 11(6): 284-292). For example, studies showed that the tpr-met fusion gene, overexpression of c-met and activated c-met mutations (collectively referred to herein as MET) all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-MET signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/MET signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

The Epidermal Growth Factor Receptor (EGFR, aka ErbB-1; HER1 in humans), is a receptor for ligands of the epidermal growth factor family. Several types of cancers are known to be dependent on EGFR over-activity or over-expression, such as lung cancer, anal cancers, glioblastoma multiforme and many other mainly epithelial cancers.

Cancer is often dependent on the genetic alteration of receptor tyrosine kinases (RTKs) e.g. by point mutation, gene amplification or chromosomal translocation which leads to uncontrolled activity of these RTKs which thus become oncogenic. Cell proliferation of cancer cells is dependent on the activity of these aberrant RTKs.

When treating the resulting proliferative diseases, often inhibitors of the oncogene RTK involved are used. However, often, after a certain time of treatment, resistance to the drug used is observed. One mechanism of resistance can involve the target RTK, compromising binding or activity of the therapeutic agent. Another mechanism is compensatory activation of an alternative kinase that continues to drive cancer growth when the primary kinase is inhibited. A well-characterized example covering both types of mechanisms is acquired resistance to the epidermal growth factor receptor (EGFR) gefitinib and erlotinib in non-small cancer (NSCLC) carrying activating EGFR mutations (see Lynch, T. J., et al., N Engl J Med, 350: 2129-2139, 2004; or Paez, J. G., et al., Science, 304: 1497-1500, 2004). For example, MET activation can compensate for loss of EGFR activity (by inhibition) by downstream activation of signal molecules such as HER3, such as MET amplification may compensate, or its ligand hepatocyte growth factor may activate MET (see Engelman, J. A., et al., Science, 316: 1039-1043, 2007; Yano, S., et al., Cancer Res, 68: 9479-9487, 2008; and Turke, A. B., et al., Cancer Cell, 17: 77-88, 2010). It is also known that MET-dependent cancer cell lines (the proliferation of which depends on the activity of MET) can be rescued from MET inhibitors by ligand-induced EGFR activation (see Bachleitner-Hofmann, T., et al, Mol Cancer Ther, 7: 3499-3508, 2008).

WO2013/149581 discloses the combination of various cMET inhibitors with various EGFR inhibitors. It relates to pharmaceutical products comprising a combination of (i) a MET inhibitor and (ii) an EGFR inhibitor, or a pharmaceutically acceptable salt or hydrate thereof, respectively, or a prodrug thereof, which are jointly active in the treatment of proliferative diseases, corresponding pharmaceutical formulations, uses, methods, processes, commercial packages and related embodiments.

SUMMARY OF THE DISCLOSURE

The present disclosure relates to pharmaceutical combination comprising (i) a MET tyrosine kinase inhibitor which is INC280 having the formula

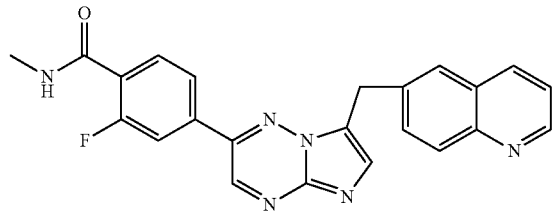 [SMILES: CNC(=O)c1ccc(-c2cnc3ncc(Cc4ccc5ncccc5c4)n3n2)cc1F]

or a pharmaceutically acceptable salt or hydrate thereof,
(ii) an EGFR tyrosine kinase inhibitor which is a compound having Formula (X) or a tautomer thereof:

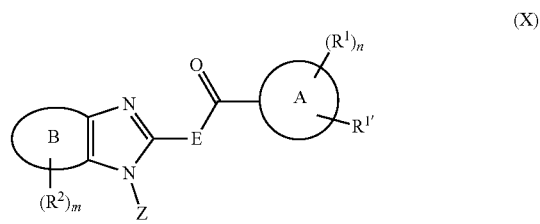

wherein Ring A is a 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Ring B is phenyl; a 5-6 membered heteroaryl comprising 1-3 heteroatoms selected from N, O and S; or a 5-6 membered heterocyclyl comprising 1-2 heteroatoms selected from N, O and S, and optionally substituted by oxo;

E is NH or $CH_2$;

$R^1$, $R^{1'}$ and $R^2$ are independently hydrogen; halo; cyano; $C_{1-6}$ alkyl; $C_{1-6}$ haloalkyl; 5-6 membered heteroaryl comprising 1-4 heteroatoms selected from N, O and S; phenyl, 5-6 membered heterocyclyl comprising 1-2 heteroatoms selected from N, O S and P, and optionally substituted by oxo; $-X^1-C(O)OR^3$; $-X^1-O-C(O)R^3$; $-X^1-C(O)R^3$; $-X^1-C(O)NR^4R^5$; $-X^1-C(O)NR^4-X^3-C(O)OR^3$; $-X^1-C(O)NR^4-X^3-S(O)_{0-2}R^6$; $-X^1-NR^4R^5$; $-X^1NR^4-X^2-C(O)R^3$; $-X^1-NR^4-X^2-C(O)OR^3$; $-X^1-NR^4-X^2-C(O)NR^4R^5$; $-X^1-NR^4-X^3-S(O)_{0-2}R^6$; $-X^1-NR^4S(O)_2R^6$; $-X^1-OS(O)_2R^6$; $-X^1-OR^3$; $-X^1-O-X^4-OR^3$; $-X^1-O-X^4-S(O)_{0-2}R^6$; $-X^1-O-X^4-NR^4R^5$; $-X^1-S(O)_{0-2}R^6$; $-X^1-S(O)_{0-2}-X^3-NR^4R^5$; $-X^1-C(O)NR^4-X^3-P(O)R^{6a}R^{6b}$; $-X^1-NR^4-X^1-P(O)R^{6a}R^{6b}$; $-X^1-O-X^1-P(O)R^{6a}R^{6b}$; $-X^1-P(O)R^{6a}-X^1-NR^4R^5$; $-X^1-P(O)R^{6a}R^{6b}$ or $-X^1-S(O)_2NR^4R^5$; wherein each phenyl, heteroaryl, or heterocyclyl in $R^1$ or $R^2$ is unsubstituted or substituted by 1-3 groups selected from OH, halo, $C_{1-6}$ alkyl, $C_{1-6}$ haloalkyl and $C_{1-6}$ haloalkoxy;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$;

$R^6$ is $C_{1-6}$ alkyl or $C_{1-6}$ haloalkyl;

$R^{6a}$ and $R^{6b}$ are independently hydroxy, $C_{1-6}$ alkyl, $C_{1-6}$ haloalkyl, $C_{1-6}$ alkoxy, $C_{1-6}$ haloalkoxy, 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Z is 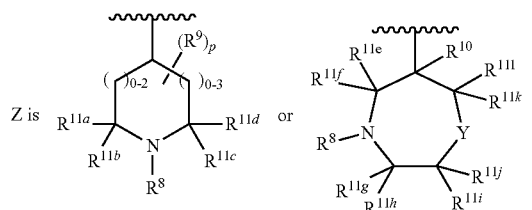

wherein Y is O or $NR^{19}$;

$R^8$ is

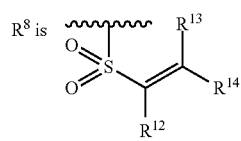 (a)

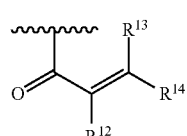 (b)

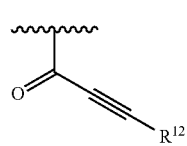 (c)

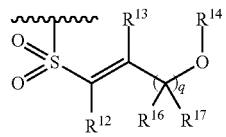 (d)

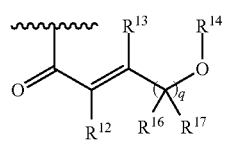 (e)

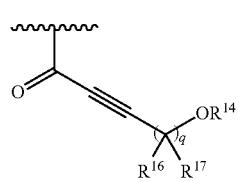 (f)

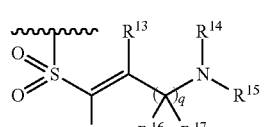 (g)

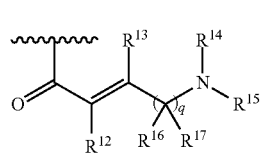 (h)

-continued

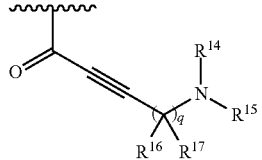 (i)

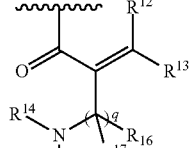 (j)

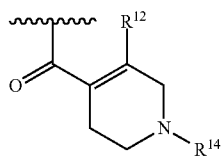 (k)

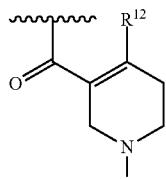 (l)

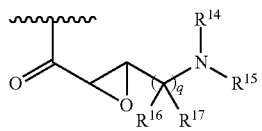 (m)

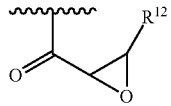 (n)

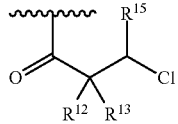 (o)

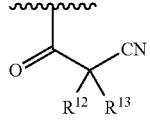 (p)

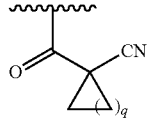 (q)

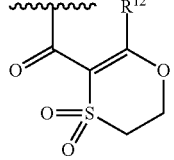 (r)

-continued

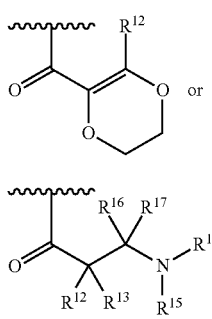

R[9] and R[10] are independently hydrogen, halo, $C_{1-6}$ alkyl, $C_{1-6}$ haloalkyl, OH, cyano, $C_{1-6}$ alkoxy, $C_{1-6}$ haloalkoxy;

R[11a], R[11b], R[11c], R[11d], R[11e], R[11f], R[11g], R[11h], R[11i], R[11j], R[11k] and R[11l] are independently hydrogen, $C_{1-6}$ alkyl or $C_{1-6}$ haloalkyl;

R[12] and R[13] are independently hydrogen, halo, cyano, $C_{1-6}$ alkyl or $C_{1-6}$ haloalkyl;

R[14] and R[15] are independently hydrogen, $C_{1-6}$ alkyl, $-L^1-R^{23}$, $-(CR^aR^b)_{2-3}-R^c$ or $-L^2-R^d$; or R[14] and R[15] together with N in $NR^{14}R^{15}$ may form a 4-7 membered ring containing 1-2 heteroatoms selected from N, O, S and P, and optionally substituted with 1-4 R[18] groups;

R[16] and R[17] are independently hydrogen or $C_{1-6}$ alkyl; or R[16] and R[17] together with the carbon to which they are attached may form a $C_{3-6}$ cycloalkyl;

$X^1$ and $X^2$ are independently a bond or $C_{1-6}$ alkyl;
$X^3$ is $C_{1-6}$ alkyl;
$X^4$ is $C_{2-6}$ alkyl;
R[19] hydrogen, $C_{1-6}$ alkyl, $COR^{20}$, $COOR^{20}$, $CONR^{20}R^{21}$ or $S(O)_2R^{20}$;
R[20] is $C_{1-6}$ alkyl, $C_{1-6}$ haloalkyl or cycloalkyl;
R[21] is hydrogen or $C_{1-6}$ alkyl; or R[20] and R[21] together with the N in $NR^{20}R^{21}$ may form a 4-7 membered ring containing 1-2 heteroatoms selected from N, O, S, P and optionally substituted with 1-4 R[22] groups;
R[7], R[18] and R[22] are independently oxo, halo, hydroxy, $C_{1-6}$ alkyl, $C_{1-6}$ haloalkyl, $C_{1-6}$ alkoxy or $C_{1-6}$ haloalkoxy;
R[23] is independently $C_{3-7}$ cycloalkyl, or a 4-10 membered heterocyclyl comprising 1-3 heteroatoms selected from N, O and S, and is optionally substituted with oxo; and R[23] is unsubstituted or substituted with $C_{1-6}$ alkyl, $C_{1-6}$ haloalkyl, $-L^3-R^e$ or $-L^4-R^f$;
$R^c$ and $R^e$ are independently halo, cyano, hydroxy, $-OR^{24}$, $-NRR^{25}$, $-NR-CO_2R^{24}$, $-NR-SO_2-R^{26}$, $-NR-COR^{26}$, $-NR-C(O)-NRR^{25}$, $-OC(O)-NRR^{25}$, or $C_{1-6}$ alkyl substituted with halo, $C_{1-6}$ alkoxy, hydroxy or cyano;
$R^d$ and $R^f$ are independently $-SO_2NRR^{25}$, $-CONRR^{25}$, $-C(O)OR^{24}$, $-SO_2R^{26}$ or $C(O)R^{26}$;
R[24] is $C_{1-6}$ alkyl, $C_{1-6}$ haloalkyl, $-L^2-R^{23a}$ or $-(CR^aR^b)_{2-3}-N(R^aR^b)_2$;
R[25] is hydrogen, $C_{1-6}$ alkyl, $C_{1-6}$ haloalkyl, $-L^2-R^{23b}$ or $-(CR_2)_{2-3}-N(R^aR^b)_2$;
R[26] is $C_{1-6}$ alkyl, $C_{1-6}$ haloalkyl, $-L^2-R^{23c}$ or $-(CR^aR^b)_{1-3}-N(R^aR^b)_2$;
R[23a], R[23b] and R[23c] are independently selected from R[23];
R, $R^a$ and $R^b$ are independently hydrogen or $C_{1-6}$ alkyl;
$L^1$, $L^2$, $L^3$ and $L^4$ are independently a bond or $-(CR^aR^b)_{1-3}$; and
n and m are independently 1-3; and p and q are 1-4; or a pharmaceutically acceptable salt thereof, and
(iiii) at least one pharmaceutically acceptable carrier.

The present disclosure also relates to a pharmaceutical combination comprising
(i) a MET tyrosine kinase inhibitor which is INC280 having the formula

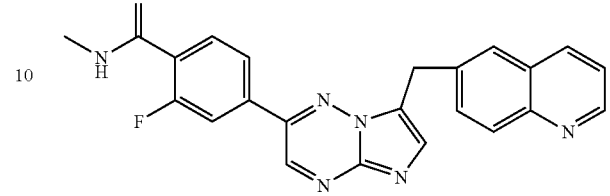

or a pharmaceutically acceptable salt or hydrate thereof,
(ii) an EGFR tyrosine kinase inhibitor which is a compound having Formula (X) or a tautomer thereof:

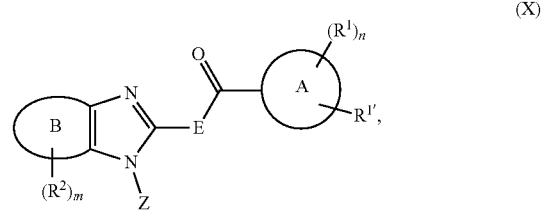

as described above, or pharmaceutically acceptable salt thereof.

In one embodiment of the combination, the EGFR tyrosine kinase inhibitor is Compound A which has the chemical name (R,E)-N-(7-chloro-1-(1-(4-(dimethylamino)but-2-enoyl)azepan-3-yl)-1H-benzo[d]imidazol-2-yl)-2-methylisonicotinamide and has the structure (Compound A)

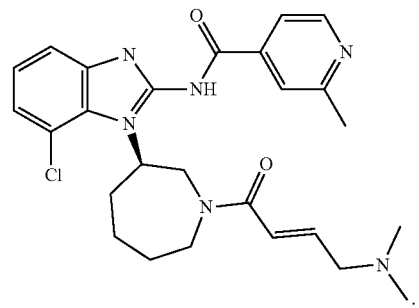

The EGFR tyrosine kinase inhibitor(s) of the present disclosure are described in detail in WO2013/184757. In particular, Compound A is described as Example 5 of WO2013/184757.

In one embodiment of the combination, the INC280 is in its dihydrochloric acid salt form.

In another embodiment, the INC280 is in the form of the dihydrochloride monohydrate salt.

In one embodiment of the combination, the MET tyrosine kinase inhibitor and the EGFR tyrosine kinase inhibitor are simultaneously, separately or sequentially administered.

The present disclosure also relates to a method of treating an EGFR tyrosine kinase activity and/or MET tyrosine kinase activity mediated disease, especially a cancer, comprising administering a pharmaceutical combination comprising
(i) a MET tyrosine kinase inhibitor which is INC280 having the formula

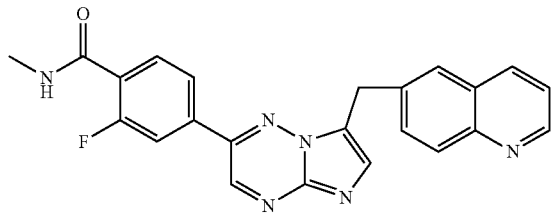 [SMILES: CNC(=O)c1ccc(-c2cnc3ncc(Cc4ccc5ncccc5c4)n3n2)cc1F]

or a pharmaceutically acceptable salt or hydrate thereof,
(ii) an EGFR tyrosine kinase inhibitor which is A compound having Formula (X) or a tautomer thereof:

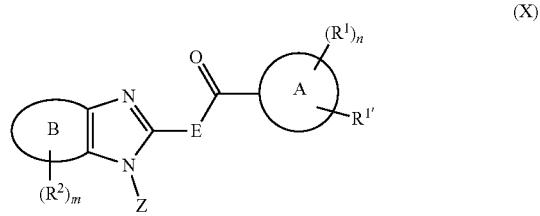

(X)

wherein Ring A is a 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Ring B is phenyl; a 5-6 membered heteroaryl comprising 1-3 heteroatoms selected from N, O and S; or a 5-6 membered heterocyclyl comprising 1-2 heteroatoms selected from N, O and S, and optionally substituted by oxo;

E is NH or $CH_2$;

$R^1$, $R^{1'}$ and $R^2$ are independently hydrogen; halo; cyano; $C_{1-6}$ alkyl; $C_{1-6}$ haloalkyl; 5-6 membered heteroaryl comprising 1-4 heteroatoms selected from N, O and S; phenyl; 5-6 membered heterocyclyl comprising 1-2 heteroatoms selected from N, O, S and P, and optionally substituted by oxo; $-X^1-C(O)OR^3$; $-X^1-O-C(O)R^3$; $-X^1-C(O)R^3$; $-X^1-C(O)NR^4R^5$; $-X^1-C(O)NR^4-X^3-C(O)OR^3$; $-X^1-C(O)NR^4-X^3-S(O)_{0-2}R^6$; $-X^1-NR^4R^5$; $-X^1NR^4-X^2-C(O)R^3$; $-X^1-NR^4-X^2-C(O)OR^3$; $-X^1-NR^4-X^2-C(O)NR^4R^5$; $-X^1-NR^4-X^3-S(O)_{0-2}R^6$; $-X^1-NR^4S(O)_2R^6$; $-X^1-OS(O)_2R^6$; $-X^1-OR^3$; $-X^1-O-X^4-OR^3$; $-X^1-O-X^4-S(O)_{0-2}R^6$; $-X^1-O-X^4-NR^4R^5$; $-X^1-S(O)_{0-2}R^6$; $-X^1-S(O)_{0-2}-X^3-NR^4R^5$; $-X^1-C(O)NR^4-X^3-P(O)R^{6a}R^{6b}$; $-X^1-NR^4-X^1-P(O)R^{6a}R^{6b}$; $-X^1-O-X^1-P(O)R^{6a}R^{6b}$; $-X^1-P(O)R^{6a}-X^1-NR^4R^5$; $-X^1-P(O)R^{6a}R^{6b}$ or $-X^1-S(O)_2NR^4R^5$; wherein each phenyl, heteroaryl, or heterocyclyl in $R^1$ or $R^2$ is unsubstituted or substituted by 1-3 groups selected from OH, halo, $C_{1-6}$ alkyl, $C_{1-6}$ haloalkyl and $C_{1-6}$ haloalkoxy;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$;

$R^6$ is $C_{1-6}$ alkyl or $C_{1-6}$ haloalkyl;

$R^{6a}$ and $R^{6b}$ are independently hydroxy, $C_{1-6}$ alkyl, $C_{1-6}$ haloalkyl, $C_{1-6}$ alkoxy, $C_{1-6}$ haloalkoxy, 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Z is

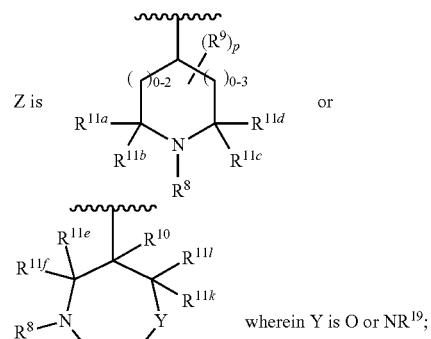

wherein Y is O or $NR^{19}$;

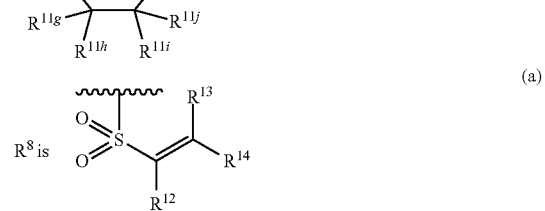
(a)

(b)

(c)

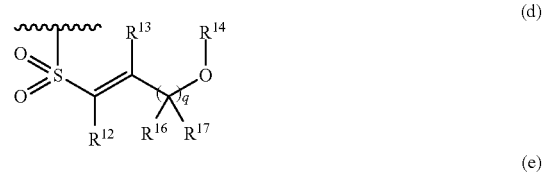
(d)

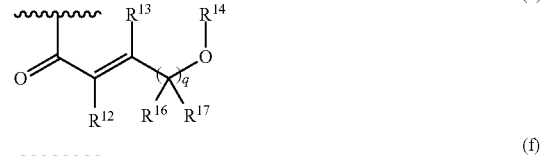
(e)

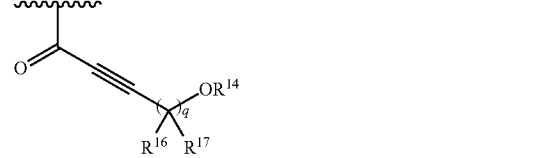
(f)

(g)

-continued

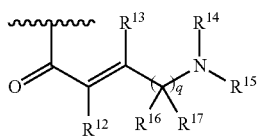 (h)

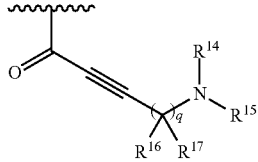 (i)

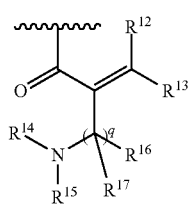 (j)

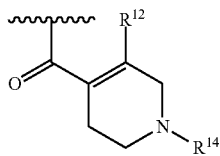 (k)

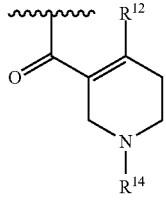 (l)

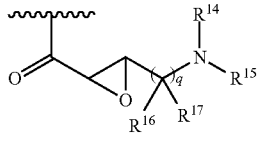 (m)

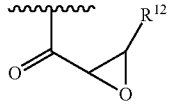 (n)

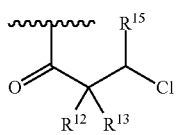 (o)

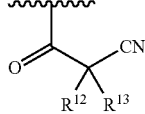 (p)

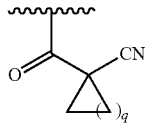 (q)

-continued

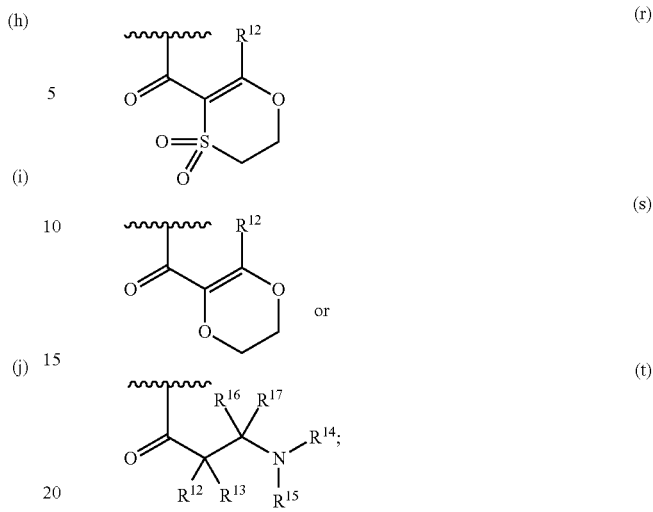

(r)

(s) or (t)

$R^9$ and $R^{10}$ are independently hydrogen, halo, $C_{1-6}$ alkyl, $C_{1-6}$ haloalkyl, OH, cyano, $C_{1-6}$ alkoxy, $C_{1-6}$ haloalkoxy;

$R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$ and $R^{11l}$ are independently hydrogen, $C_{1-6}$ alkyl or $C_{1-6}$ haloalkyl;

$R^{12}$ and $R^{13}$ are independently hydrogen, halo, cyano, $C_{1-6}$ alkyl or $C_{1-6}$ haloalkyl;

$R^{14}$ and $R^{15}$ are independently hydrogen, $C_{1-6}$ alkyl, -L$^1$-$R^{23}$, —(CR$^a$R$^b$)$_{2-3}$—R$^c$ or -L$^2$-R$^d$; or $R^{14}$ and $R^{15}$ together with N in NR$^{14}$R$^{15}$ may form a 4-7 membered ring containing 1-2 heteroatoms selected from N, O, S and P, and optionally substituted with 1-4 $R^{18}$ groups;

$R^{16}$ and $R^{17}$ are independently hydrogen or $C_{1-6}$ alkyl; or $R^{16}$ and $R^{17}$ together with the carbon to which they are attached may form a $C_{3-6}$ cycloalkyl;

$X^1$ and $X^2$ are independently a bond or $C_{1-6}$ alkyl;

$X^3$ is $C_{1-6}$ alkyl;

$X^4$ is $C_{2-6}$ alkyl;

$R^{19}$ hydrogen, $C_{1-6}$ alkyl, COR$^{20}$, COOR$^{20}$, CONR$^{20}$R$^{21}$ or S(O)$_2$R$^{20}$;

$R^{20}$ is $C_{1-6}$ alkyl, $C_{1-6}$ haloalkyl or cycloalkyl;

$R^{21}$ is hydrogen or $C_{1-6}$ alkyl; or $R^{20}$ and $R^{21}$ together with the N in NR$^{20}$R$^{21}$ may form a 4-7 membered ring containing 1-2 heteroatoms selected from N, O, S, P and optionally substituted with 1-4 $R^{22}$ groups;

$R^7$, $R^{18}$ and $R^{22}$ are independently oxo, halo, hydroxy, $C_{1-6}$ alkyl, $C_{1-6}$ haloalkyl, $C_{1-6}$ alkoxy or $C_{1-6}$ haloalkoxy;

$R^{23}$ is independently $C_{3-7}$ cycloalkyl, or a 4-10 membered heterocyclyl comprising 1-3 heteroatoms selected from N, O and S, and is optionally substituted with oxo; and $R^{23}$ is unsubstituted or substituted with $C_{1-6}$ alkyl, $C_{1-6}$ haloalkyl, -L$^3$-R$^e$ or -L$^4$-R$^f$;

$R^c$ and $R^e$ are independently halo, cyano, hydroxy, —OR$^{24}$, —NRR$^{25}$, —NR—CO$_2$R$^{24}$, —NR—SO$_2$—R$^{26}$, —NR—COR$^{26}$, —NR—C(O)—NRR$^{25}$, —OC(O)—NRR$^{25}$, or $C_{1-6}$ alkyl substituted with halo, $C_{1-6}$ alkoxy, hydroxy or cyano;

$R^d$ and $R^f$ are independently —SO$_2$NRR$^{25}$, —CONRR$^{25}$, —C(O)OR$^{24}$, —SO$_2$R$^{26}$ or C(O)R$^{26}$;

$R^{24}$ is $C_{1-6}$ alkyl, $C_{1-6}$haloalkyl, -L$^2$-R$^{23a}$ or —(CR$^a$R$^b$)$_{2-3}$—N(R$^a$R$^b$)$_2$;

$R^{25}$ is hydrogen, $C_{1-6}$ alkyl, $C_{1-6}$haloalkyl, -L$^2$-R$^{23b}$ or —(CR$_2$)$_{2-3}$—N(R$^a$R$^b$)$_2$;

$R^{26}$ is $C_{1-6}$ alkyl, $C_{1-6}$haloalkyl, -L$^2$-R$^{23c}$ or —(CR$^a$R$^b$)$_{1-3}$—N(R$^a$R$^b$)$_2$;

$R^{23a}$, $R^{23b}$ and $R^{23c}$ are independently selected from $R^{23}$;
R, $R^a$ and $R^b$ are independently hydrogen or $C_{1-6}$ alkyl;
$L^1$, $L^2$, $L^3$ and $L^4$ are independently a bond or —$(CR^a R^b)_{1-3}$; and
n and m are independently 1-3; and p and q are 1-4;
or a pharmaceutically acceptable salt thereof, and
(iiii) optionally at least one pharmaceutically acceptable carrier.

In one embodiment of the method, the EGFR tyrosine kinase inhibitor is Compound A which has the chemical name (R,E)-N-(7-chloro-1-(1-(4-(dimethylamino)but-2-enoyl)azepan-3-yl)-1H-benzo[d]imidazol-2-yl)-2-methyl-isonicotinamide and has the structure (Compound A)

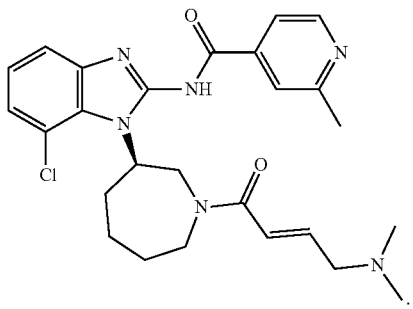

Compound A may be in a pharmaceutically acceptable form, e.g the hydrochloric acid salt form or a mesylate salt form.

In one embodiment of the method, the INC280 is in its dihydrochloric acid salt form.

In another embodiment, the INC280 is in the form of the dihydrochloride monohydrate salt.

In one embodiment of the method, the MET tyrosine kinase inhibitor and the EGFR tyrosine kinase inhibitor are simultaneously, separately or sequentially administered.

In one embodiment of the method, the cancer is selected from the group consisting of carcinomas (e.g., bladder, breast, cervical, cholangiocarcinoma, colorectal, esophageal, gastric, head and neck, kidney, liver, lung, nasopharyngeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor.

In one embodiment of the method, the cancer is non-small cell lung cancer (NSCLC).

In another embodiment of the method, the cancer is metastatic non-small cell lung cancer.

In another embodiment of the method, the cancer is colorectal cancer (CRC).

In another embodiment of the method, the cancer is metastatic colorectal cancer (mCRC).

In another embodiment of the method, the cancer is head and neck cancer.

In another embodiment of the method, the cancer is metastatic head and neck cancer.

In yet another embodiment of the method, the cancer is head and neck squamous cell carcinoma (HNSCC).

DETAILED DESCRIPTION OF THE FIGURES

FIGS. 1-4 demonstrate the effects of the combination of Compound A and INC280.

FIG. 5 illustrates donor study and confirmation of Erlotinib resistant NCI-HCC827 xenograft model.

FIG. 6 illustrates confirmation of phospho MET activity by pRTK analysis.

FIG. 7 illustrates donor study and confirmation of Compound A resistant NCI-HCC827 xenograft model.

FIG. 8 illustrates the confirmation of phospho MET activity by pRTK analysis.

FIG. 9 illustrates PD western using tumor lysates shows selective depletion of pEGFR and pMET expression using Compound A and or INC280.

FIG. 10 illustrates the in vivo efficacy of compound A in combination with INC280 in an compound A resistant NCI-HCC827 mouse xenograft model.

FIG. 11 shows percent body weight change in the combination study.

FIG. 12 illustrates IHC and histology results.

DETAILED DESCRIPTION OF THE DISCLOSURE

Figure 1:
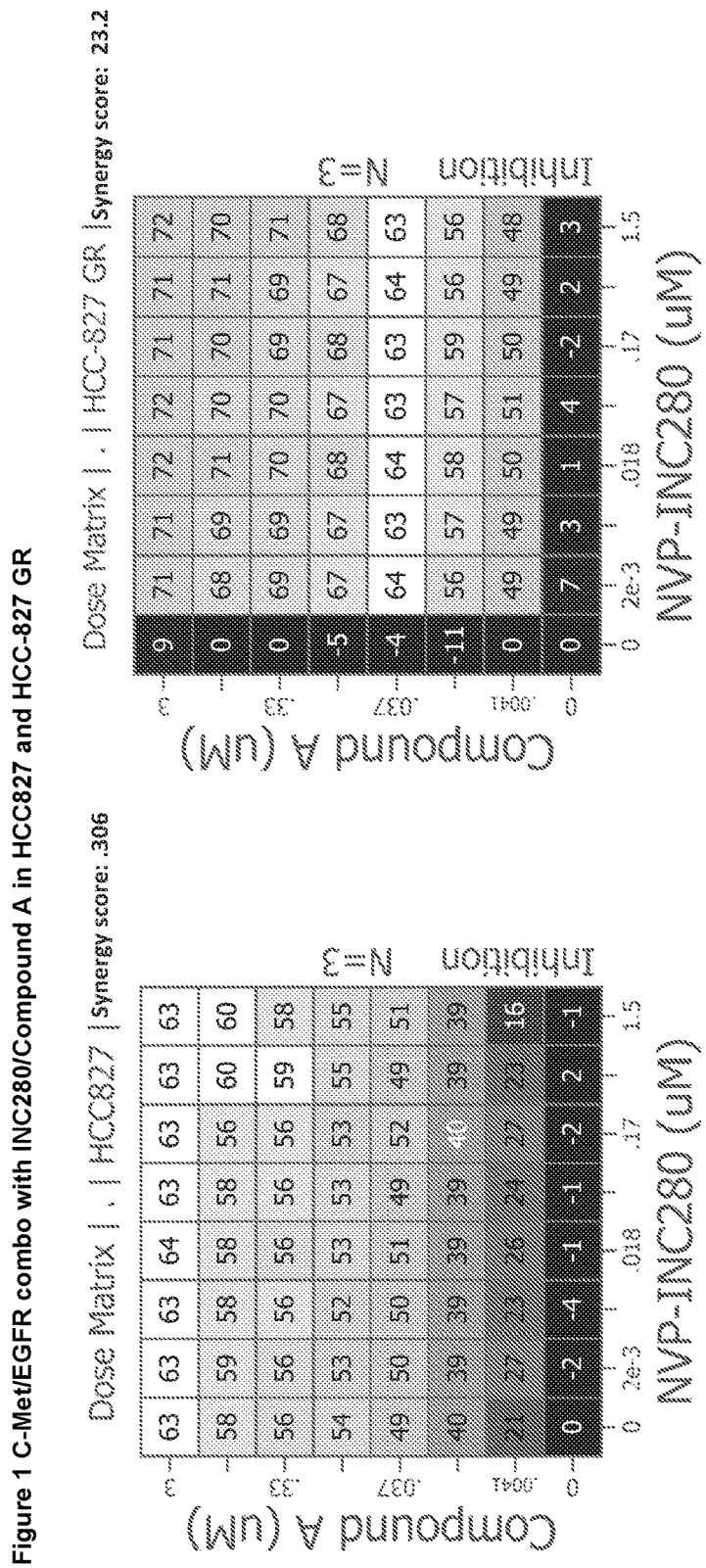

The present disclosure relates to a pharmaceutical combination (e.g. combination product) comprising (i) a MET inhibitor which is INC280 or a pharmaceutically acceptable salt or hydrate and (ii) an EGFR inhibitor of Formula (X), e.g. Compound A, as described herein.

The present disclosure, according to one embodiment, relates to a pharmaceutical combination (e.g. combination product) comprising (i) a MET inhibitor which is INC280 or a pharmaceutically acceptable salt and (ii) an EGFR inhibitor of Formula (X) described herein or a pharmaceutically acceptable salt and at least one pharmaceutically acceptable carrier.

A preferred EGFR inhibitor of Formula (X) is Compound A, or a pharmaceutically acceptable salt thereof. Compound A may be in the free form (i.e. not a salt) Alternatively, Compound A may be present as a salt. Compound A may be present as the hydrochloride salt or the mesylate (methylsulphonate) salt, more preferably as the mono-mesylate salt. Said mesylate salts may be in an amorphous of crystalline state. A particularly useful salt form of Compound A is the mono-mesylate trihydrate salt thereof. Free forms and salt forms of Compound A are described in PCT application PCT/IB2014/066475, which published as WO/2015/083059.

The chemical name of INC280 is 2-fluoro-N-methyl-4-[(7-quinolin-6-yl-methyl)-imidazo[1,2-b]triazin-2-yl]benzamide which has the formula

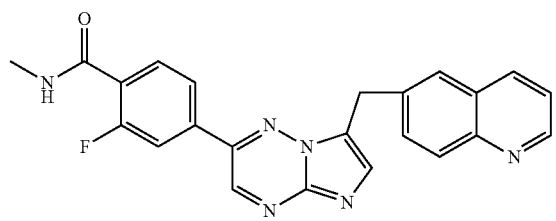 [SMILES: CNC(=O)c1ccc(-c2cnc3ncc(Cc4ccc5ncccc5c4)n3n2)cc1F]

INC280 is disclosed in WO 2008/064157, Example 7. Non-limiting examples of salt forms of INC280 are dihydrochloric acid form and dibenzenesulfonic acid salts. In particular, INC280 can be in the form of the dihydrochloride monohydrate salt (also described in U.S. Pat. No. 8,420,645). INC280 is also known by its INN which is capmatinib.

A further embodiment of this disclosure provides a combination (e.g. combination product) comprising a quantity which is jointly therapeutically effective against an EGFR tyrosine kinase activity and/or MET tyrosine kinase activity mediated disease, especially a cancer, comprising the combination partners (i) EGFR tyrosine kinase inhibitor which is of Formula (X) described herein or a pharmaceutically acceptable salt and (ii) MET tyrosine kinase inhibitor which is INC280 or a pharmaceutically acceptable salt thereof, and optionally at least one pharmaceutically acceptable carrier material.

A further embodiment relates to the use of the inventive combination (e.g. combination product) for treating an EGFR tyrosine kinase activity and/or MET tyrosine kinase activity mediated disease, especially a cancer.

There is also provided a combination as described herein, for use in treating an EGFR tyrosine kinase activity and/or MET tyrosine kinase activity mediated disease, especially a cancer. The combination may be a fixed combination or a non-fixed combination.

A further embodiment relates to the use of a combination of (i) an EGFR tyrosine kinase inhibitor which of Formula (X) described herein, e.g. Compound A, or a pharmaceutically acceptable salt and (ii) a MET tyrosine kinase inhibitor which is INC280 or a pharmaceutically acceptable salt thereof, for the manufacture of a medicament or a pharmaceutical product for treating an EGFR tyrosine kinase activity and/or MET tyrosine kinase activity mediated disease, especially a cancer.

A further embodiment relates to a method of treating an EGFR tyrosine kinase activity and/or MET tyrosine kinase activity mediated disease, especially a cancer, with a combination of (i) an EGFR tyrosine kinase inhibitor which is of Formula (X) described herein, e.g. Compound A, or a pharmaceutically acceptable salt and (ii) a MET tyrosine kinase inhibitor which is INC280 or a pharmaceutically acceptable salt thereof.

A further embodiment relates to a method for the treatment of an EGFR tyrosine kinase activity and/or MET tyrosine kinase activity mediated disease, especially a cancer, said method comprising administering an effective amount of a combination or a combination product comprising (i) an EGFR tyrosine kinase inhibitor which is of Formula (X) described herein, e.g. Compound A, or a pharmaceutically acceptable salt and (ii) a MET tyrosine kinase inhibitor which is INC280 or a pharmaceutically acceptable salt thereof to a subject in need thereof, such as a warm-blooded animal, in particular a human.

Yet a further embodiment of present disclosure relates to a pharmaceutical product or a commercial package comprising a combination product according to the disclosure described herein, in particular together with instructions for simultaneous, separate or sequential use (especially for being jointly active) thereof in the treatment of an EGFR tyrosine kinase activity and/or MET tyrosine kinase activity mediated disease, especially a cancer, in particular for use in the treatment of an EGFR tyrosine kinase activity and/or MET tyrosine kinase activity mediated disease, especially a cancer.

A further embodiment of present disclosure relates to the use of (i) an EGFR tyrosine kinase inhibitor which is of Formula (X) described herein or a pharmaceutically acceptable salt thereof and (ii) a MET tyrosine kinase inhibitor which is INC280 or a pharmaceutically acceptable salt thereof, for the preparation of a combination (e.g. a combination product) according to present disclosure.

The following definitions show more specific embodiments of general features or expressions which can be used to replace one, more than one or all general features or expressions in the embodiments described hereinbefore and hereinafter, thus leading to more specific embodiments.

Definitions

The term "C1-6 alkyl" as used herein denotes a saturated or unsaturated alkyl radical having from 1 up to 6 carbon atoms, the radicals being either linear or branched with single or multiple branching; for example, butyl, such as n-butyl, sec-butyl, isobutyl, tert-butyl; propyl, such as n-propyl or isopropyl; ethyl or methyl. In particular embodiments, the C1-6 alkyl is a saturated alkyl radical, and where specified, may be unsubstituted or substituted, for example by halo (i.e., haloalkyl such as trifluoromethyl, and the like), hydroxy (hydroxyalkyl such as hydroxymethyl, hydroxyethyl, 2-hydroxy-2-propyl and the like) or cyano (cyanoalkyl such as cyanomethyl, cyanoethyl and the like).

The term "C1-6alkoxy" as used herein refers to the group —ORa, where Ra is C1-6 alkyl group as defined herein. Non-limiting examples of alkoxy groups, as used herein, include methoxy, ethoxy, n-propoxy, isopropoxy, n-butyloxy, t-butyloxy, pentyloxy, hexyloxy and the like.

The term "C1-6 haloalkyl" refers to C1-6 alkyl group as defined herein, substituted with one or more halo groups, which may be the same or different. The haloalkyl can be monohaloalkyl, dihaloalkyl or polyhaloalkyl, including perhaloalkyl. In certain embodiments, a haloalkyl group is trifluoromethyl.

The term "cycloalkyl" as used herein, refers to a saturated or unsaturated monocyclic hydrocarbon group. The terms "C3-7cycloalkyl" or "C5-6 cycloalkyl" as used herein refer to a cycloalkyl having from 3 up to 7 carbon atoms, or from 5 to 6 carbon atoms, respectively; for example, cyclopropyl, cyclobutyl, cyclopentyl, cyclohexyl or cycloheptyl.

As used herein, the term "aryl" refers to an aromatic hydrocarbon group having 6-10 carbon atoms in the ring portion, and can be a single or bicyclic aromatic ring. Non-limiting examples include phenyl, naphthyl or tetrahydronaphthyl.

The term "heteroaryl," as used herein, refers to a 5-10 membered heteroaromatic ring having 1 to 4 heteroatoms independently selected from nitrogen, oxygen and sulfur, which may be a 5-6 membered monocyclic ring or an 8-10 membered fused bicyclic ring where at least one of the rings is aromatic. Such bicyclic ring systems may be fused to one or more aryl, cycloalkyl, or heterocycloalkyl rings. Non-limiting examples of heteroaryl groups, as used herein, include 2- or 3-furyl; 1-, 2-, 4-, or 5-imidazolyl; 3-, 4-, or 5-isothiazolyl; 3-, 4-, or 5-isoxazolyl; 2-, 4-, or 5-oxazolyl; 4- or 5-1,2,3-oxadiazolyl; 2- or 3-pyrazinyl; 1-, 3-, 4-, or 5-pyrazolyl; 3-, 4-, 5- or 6-pyridazinyl; 2-, 3-, or 4-pyridyl; 2-, 4-, 5- or 6-pyrimidinyl; 1-, 2- or 3-pyrrolyl; 1- or 5-tetrazolyl; 2- or 5-1,3,4-thiadiazolyl; 2-, 4-, or 5-thiazolyl; 2- or 3-thienyl; 2-, 4- or 6-1,3,5-triazinyl; 1-, 3- or 5-1,2,4-triazolyl; 1-, 4- or 5-1,2,3-triazolyl; 2-, 4-, 5-, 6-, or 7-benzoxazolyl; 1-, 2-, 4-, 5-, 6-, or 7-benzimidazolyl; 2-, 4-, 5-, 6-, or 7-benzothiazolyl; 2-, 3-, 4-, 5-, 6-, 7-benzo[b]thienyl; 2-, 3-, 4-, 5-, 6-, 7-, 8-, 9-benzo[b]oxepine; 2-, 4-, 5-, 6-, 7-, or 8-benzoxazinyl; 1-, 2-, 3-, 4-, 5-, 6-, 7-, 8, or 9-carbazolyl; 3-, 4-, 5-, 6-, 7-, or 8-cinnolinyl; 2-, 4-, or 5-4H-imidazo[4,5-d] thiazolyl; 2-, 3-, 5-, or 6-imidazo[2,1-b] thiazolyl; 2-, 3-, 6-, or 7-imidazo[1,2-b][1,2,4]triazinyl; 1-, 3-, 4-, 5-, 6-, or 7-indazolyl; 1-, 2-, 3-, 5-, 6-, 7-, or 8-indolizinyl; 1-, 2-, 3-, 4-, 5-, 6-, or 7-indolyl; 1-, 2-, 3-, 4-, 5-, 6-, or 7-isoindolyl; 1-, 3-, 4-, 5-, 6-, 7-, or 8-isoquinolinyl; 2-, 3-, 4-, 5-, 6-, or 7-naphthyridinyl; 1-, 4-, 5-, 6-, 7-, or 8-phthalazinyl; 2-, 4-, 6-, or 7-pteridinyl; 2-, 6-, 7-, or 8-purinyl; 2-, 3-, 5-, 6-, or 7-furo[3,2-b]-pyranyl; 1-, 3-, or 5-1H-pyrazolo[4,3-d]-oxazolyl; 2-, 3-, 5-, or 8-pyrazino[2,3-d]pyridazinyl; 1-, 2-, 3-, 4-, 5-, or 8-5H-pyrido[2,3-d]-o-oxazinyl; 1-, 2-, 3-, 4-, 6-, 7-, 8-, or 9-quinolizinyl; 2-, 3-, 4-, 5-, 6-, 7-, or 8-quinolinyl; 2-, 3-, 4-, 5-, 6-, 7-, or 8-quinazolinyl; and 2-, 3-, 4-, or 5-thieno[2,3-b]furanyl.

As used herein, the terms "heterocyclyl" or "heterocyclic" refer to a saturated or unsaturated non-aromatic ring or ring system, e.g., which is a 4-, 5-, 6-, or 7 membered monocyclic, or 6-, 7-, 8-, 9-, 10-, 11-, or 12-membered bicyclic ring system and contains at least one heteroatom selected from O, S, P and N, where the N, S and P can also optionally be oxidized to various oxidation states. The heterocyclic group can be attached at a heteroatom or a carbon atom. Examples of heterocycles include tetrahydrofuran (THF), dihydrofuran, 1, 4-dioxane, morpholine, 1,4-dithiane, piperazine, piperidine, 1,3-dioxolane, imidazolidine, imidazoline, pyrroline, pyrrolidine, azetidinyl, tetrahydropyran, dihydropyran, oxathiolane, dithiolane, 1,3-dioxane, 1,3-dithiane, oxathiane, thiomorpholine, and the like. Where specified, the term "heterocyclyl" further refers to heterocyclic groups that is substituted by oxo; for example, pyrrolidin-2-one, 1,6-dihydro-pyridin-2(3H)-one, pyridin-2-(3H)-one, and the like.

The term "heteroatoms," as used herein, refers to nitrogen (N), oxygen (O), sulfur (S) or phosphorus (P) atoms, wherein the N, S and P can optionally be oxidized to various oxidation states.

Compounds useful according to the disclosure can also include all isotopes of atoms occurring in the intermediates or final compounds. Isotopes include those atoms having the same atomic number but different mass numbers. Examples of isotopes that can be incorporated into compounds of the disclosure include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. Various isotopically labeled compounds of the present disclosure, for example those into which radioactive isotopes such as $^3$H, $^{13}$C, and $^{14}$C are incorporated. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this disclosure can generally be prepared by carrying out the procedures disclosed in the schemes or in the examples and preparations described below by substituting a. readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (X) and/or compound A. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium, for example in the ranges given above.

Isotopically-labeled MET and/or EGFR tyrosine kinase inhibitor compounds forming part of a combination product according to the disclosure can generally be prepared by conventional techniques known to those skilled in the art or by processes analogous to those described in the accompanying Examples and Preparations using an appropriate isotopically-labeled reagents in place of the non-labeled reagent previously employed.

The present disclosure embodiments also include pharmaceutically acceptable salts of the compounds useful according to the disclosure described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds useful according to the disclosure (=being included in a combination, especially a combination product, according to the disclosure, respectively, or being used according to the disclosure, optionally also including further co-agents as defined below, that is, all active ingredients), as well as their pharmaceutically acceptable salts, can also be present as tautomers, N-oxides or solvates, e.g. hydrates. All these variants, as well as any single one thereof or combination of two or more to less than all such variants, are encompassed and to be read herein where a compound included in the inventive combination products, e.g. an EGFR tyrosine kinase inhibitor and/or a MET tyrosine kinase inhibitor, is mentioned.

The present disclosure, according to an embodiment mentioned above and below, relates to a pharmaceutical combination, especially a pharmaceutical combination product, comprising the mentioned combination partners and at least one pharmaceutically acceptable carrier.

The present disclosure also provides a pharmaceutical combination, especially a pharmaceutical combination product, comprising the mentioned combination partners.

"Combination" refers to formulations of the separate partners with or without instructions for combined use or to combination products. The combination partners may thus be entirely separate pharmaceutical dosage forms or pharmaceutical compositions that are also sold independently of each other and where just instructions for their combined use are provided in the package equipment, e.g. leaflet or the like, or in other information e.g. provided to physicians and medical staff (e.g. oral communications, communications in writing or the like), for simultaneous or sequential use for being jointly active, especially as defined below.

"Combination product" refers especially to either a fixed combination in one dosage unit form, or a kit of parts for the combined administration where an EGFR tyrosine kinase inhibitor and a MET tyrosine kinase inhibitor (and optionally yet a further combination partner (e.g. an other drug as explained below, also referred to as "co-agent") may be administered independently at the same time or separately within time intervals, especially where these time intervals allow that the combination partners show a cooperative (=joint), e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration and/or at the same time. The term "combination product" as used herein thus means a pharmaceutical product that results from the mixing or combining of more than one active ingredient and includes both fixed and non-fixed combinations of the active ingredients (which may also be combined).

The term "fixed combination" means that the active ingredients, e.g. an EGFR tyrosine kinase inhibitor and MET tyrosine kinase inhibitor, are both administered to a patient simultaneously in the form of a single entity or dosage. In other terms: the active ingredients are present in one dosage form, e.g. in one tablet or in one capsule.

The term "non-fixed combination" means that the active ingredients are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients. The term "non-fixed combination" thus defines especially a "kit of parts" in the sense that the combination partners (i) EGFR tyrosine kinase inhibitor and (ii) MET tyrosine kinase inhibitor (and if present further one or more co-agents) as defined herein can be dosed independently of each other or by use of different fixed combinations with distinguished amounts of the combination partners, i.e. simultaneously or at different time points, where the combination partners may also be used as entirely separate pharmaceutical dosage forms or pharmaceutical formulations that are also sold independently of each other and just instructions of the possibility of their combined use is or are provided in the package equipment, e.g. leaflet or the like, or in other information e.g. provided to physicians and medical staff. The independent formulations or the parts of the kit of parts can then, e.g. be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (i) and (ii), thus being jointly active. The ratio of the total amounts of the combination partner (i) to the combination partner (ii) to be administered in the combined preparation can be varied, e.g. in order to cope with the needs of a patient sub-population to be treated or the needs of the single patient which different needs can be due to age, sex, body weight, etc. of the patients.

The disclosure also relates to (i) a MET inhibitor which is INC280 or a pharmaceutically acceptable salt thereof and (ii) an EGFR inhibitor which is of Formula (X) described herein or a pharmaceutically acceptable salt thereof, for combined use in a method of treating an EGFR tyrosine kinase activity and/or MET tyrosine kinase activity mediated disease, especially a cancer.

The combination partners (i) and (ii) in any embodiment are preferably formulated or used to be jointly (prophylactically or especially therapeutically) active. This means in particular that there is at least one beneficial effect, e.g. a mutual enhancing of the effect of the combination partners (i) and (ii), in particular a synergism, e.g. a more than additive effect, additional advantageous effects (e.g. a further therapeutic effect not found for any of the single compounds), less side effects, a combined therapeutic effect in a non-effective dosage of one or both of the combination partners (i) and (ii), and very preferably a clear synergism of the combination partners (i) and (ii). For example, the term "jointly (therapeutically) active" may mean that the compounds may be given separately or sequentially (in a chronologically staggered manner, especially a sequence-specific manner) in such time intervals that they preferably, in the warm-blooded animal, especially human, to be treated, and still show a (preferably synergistic) interaction (joint therapeutic effect). A joint therapeutic effect can, inter alia, be determined by following the blood levels, showing that both compounds are present in the blood of the human to be treated at least during certain time intervals, but this is not to exclude the case where the compounds are jointly active although they are not present in blood simultaneously.

The present disclosure thus pertains to a combination product for simultaneous, separate or sequential use, such as a combined preparation or a pharmaceutical fixed combination, or a combination of such preparation and combination.

In the combination therapies of the disclosure, the compounds useful according to the disclosure may be manufactured and/or formulated by the same or different manufacturers. Moreover, the combination partners may be brought together into a combination therapy: (i) prior to release of the combination product to physicians (e.g. in the case of a kit comprising the compound of the disclosure and the other therapeutic agent); (ii) by the physician themselves (or under the guidance of a physician) shortly before administration; (iii) in the patient themselves, e.g. during sequential administration of the compound of the disclosure and the other therapeutic agent.

In certain embodiments, any of the above methods involve further administering one or more other (e.g. third) co-agents, especially a chemotherapeutic agent.

Thus, the disclosure relates in a further embodiment to a combination product, particularly a pharmaceutical composition, comprising a therapeutically effective amount of (i) an EGFR tyrosine kinase inhibitor which is of Formula (X) described herein or a pharmaceutically acceptable salt and (ii) a MET tyrosine kinase inhibitor which is INC280 or a pharmaceutically acceptable salt thereof, and at least one third therapeutically active agent (co-agent), e.g. another compound (i) and/or (ii) or a different co-agent. The additional co-agent is preferably selected from the group consisting of an anti-cancer agent; an anti-inflammatory agent.

Also in this case, the combination partners forming a corresponding product according to the disclosure may be mixed to form a fixed pharmaceutical composition or they may be administered separately or pairwise (i.e. before, simultaneously with or after the other drug substance(s)).

A combination product according to the disclosure can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Possible anti-cancer agents (e.g. for chemotherapy) as co-agents include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; kinesin spindle protein inhibitors; MEK inhibitors; leucovorin; EDG binders; antileukemia compounds; ribonucleotide reductase inhibitors; S-adenosylmethionine decarboxylase inhibitors; angiostatic steroids; corticosteroids; other chemotherapeutic compounds (as defined below); photosensitizing compounds.

Further, alternatively or in addition combination products according to the disclosure may be used in combination with other tumor treatment approaches, including surgery, ionizing radiation, photodynamic therapy, implants, e.g. with corticosteroids, hormones, or they may be used as radiosensitizers.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, rogletimide, pyridoglutethimide, trilostane, testolactone, ketoconazole, vorozole, fadrozole, anastrozole and letrozole.

The term "antiestrogen" as used herein relates to a compound which antagonizes the effect of estrogens at the estrogen receptor level. The term includes, but is not limited to tamoxifen, fulvestrant, raloxifene and raloxifene hydrochloride.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804).

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof.

The term "alkylating compound" as used herein includes, but is not limited to, cyclophosphamide, ifosfamide, melphalan or nitrosourea (BCNU or Gliadel).

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed.

The term "platin compound" as used herein includes, but is not limited to, carboplatin, cis-platin, cisplatinum and oxaliplatin.

The term "compounds targeting/decreasing a protein or lipid kinase activity"; or a "protein or lipid phosphatase activity"; or "further anti-angiogenic compounds" as used herein includes, but is not limited to, c-Met tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

c) compounds targeting, decreasing or inhibiting the activity of the Trk receptor tyrosine kinase family, or ephrin kinase family inhibitors;

d) compounds targeting, decreasing or inhibiting the activity of the Axl receptor tyrosine kinase family;

e) compounds targeting, decreasing or inhibiting the activity of the Ret receptor tyrosine kinase;

f) compounds targeting, decreasing or inhibiting the activity of the Kit/SCFR receptor tyrosine kinase, e.g. imatinib;

g) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of the Ron receptor tyrosine kinase.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof. The term "Compounds which induce cell differentiation processes" includes, but is not limited to e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxibThe term "bisphosphonates" as used herein includes, but is not limited to, etridonic, clodronic, tiludronic, pamidronic, alendronic, ibandronic, risedronic and zoledronic acid.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide, AUY922 from Novartis.

The term "antiproliferative antibodies" as used herein includes, but is not limited to erbitux, bevacizumab, rituximab, PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "EDG binders" as used herein refers a class of immunosuppressants that modulates lymphocyte recirculation, such as FTY720.

The term "kinesin spindle protein inhibitors" is known in the field and includes SB715992 or SB743921 from GlaxoSmithKline, pentamidine/chlorpromazine from CombinatoRx.

The term "MEK inhibitors" is known in the field and includes ARRY142886 from Array PioPharma, AZD6244 from AstraZeneca, PD181461 from Pfizer, leucovorin.

The term "ribonucleotide reductase inhibitors" includes, but is not limited to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF/VEGFR disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab.

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Corticosteroids" as used herein includes, but is not limited to compounds, such as e.g. fluocinolone, dexamethasone; in particular in the form of implants.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

A combination product according to the disclosure may also be used in combination with or comprise one or more further drug substances selected from the group of anti-inflammatory drug substances; antihistamine drug substances; bronchodilatatory drug substances, NSAID; antagonists of chemokine receptors.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, and WO 04/005229.

LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such as cilomilast, Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

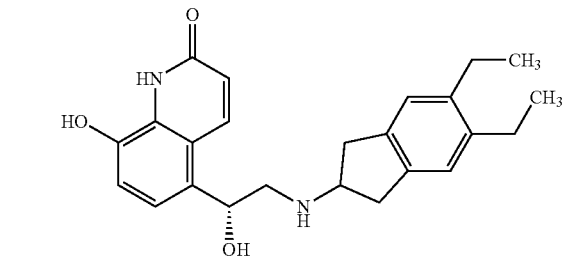 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable chemokine receptors include, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N—[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The term "pharmaceutically effective" preferably relates to an amount that is therapeutically or in a broader sense also prophylactically effective against the progression of a disease or disorder as disclosed herein.

The term "a commercial package" as used herein defines especially a "kit of parts" in the sense that the components (a) MET tyrosine kinase inhibitor and (b) EGFR tyrosine kinase inhibitor as defined above and below, and optionally further co-agents, can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronologically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal effect) or the like.

The combination products according to the present disclosure are appropriate for the treatment of various diseases that are mediated by, especially depend on, the activity of EGFR and/or MET tyrosine kinase, respectively. They can thus be used in the treatment of any of the diseases that can be treated by EGFR tyrosine kinase inhibitors and MET tyrosine kinase inhibitors.

The combination of the present disclosure may be particularly useful for the treatment of a cancer wherein the cancer is an EGFR resistant tumor with a c-MET activation/amplification. For example, the cancer may be non-small cell lung cancer (NSCLC) or metastatic non-small cell lung cancer.

The combination of the present disclosure may be particularly useful the cancer (e.g. NSCLC) when the cancer fails to respond to previous treatment, e.g with Compound A, with erlotinib, gefitinib or afatinib. Thus the cancer to be treated may have been found to be resistant to treatment with a therapeutic agent which is selected from the group consisting of erlotinib, gefitinib., afatinib, Compound A or a combination thereof.

EGFR inhibitors are e.g. useful in the treatment of one or more of the diseases which respond to an inhibition of EGFR activity, especially a neoplastic or tumor disease, especially solid tumor, more especially those cancers in which EGFR kinases are implicated including breast cancer, gastric cancer, lung cancer, cancer of the prostate, bladder cancer and endometrial cancer. Further cancers include cancer of the kidney, liver, adrenal glands, stomach, ovaries, colon, rectum, pancreas, vagina or thyroid, sarcoma, glioblastomas and numerous tumours of the neck and head, as well as leukemias and multiple myeloma. Especially preferred are cancers of breast or ovary; lung cancer, e.g. NSCLC or SCLC; head and neck, renal, colorectal, pancreas, bladder, gastric or prostate cancer; or glioma; in particular, glioma or colon, rectum or colorectal cancer or more particularly lung cancer are to be mentioned. Also diseases dependent on ligands of EGFR, such as EGF; TGF-α; HB-EGF; amphiregulin; epiregulin; betacellulin, are included.

MET inhibitors are e.g. useful in the treatment of MET related diseases, especially cancers that display evidence for simultaneous activation of MET and FGFR, including gene amplification, activating mutations, expression of cognate RTK ligands, phosphorylation of RTKs at residues indicative of activation, e.g. where the cancer is selected from the group consisting of brain cancer, stomach cancer, genital cancer, urinary cancer, prostate cancer, (urinary) bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and (e.g. embryonal) rhabdomyosarcomas, alveolar soft part sarcomas); thyroid carcinoma (papillary and other subtypes).

MET inhibitors are e.g. also useful in the treatment of cancer wherein the cancer is stomach, colon, liver, genital, urinary, melanoma, or prostate. In a particular embodiment, the cancer is liver or esophageal.

MET inhibitors are e.g. also useful in the treatment of colon cancer, including metastases, e.g. in the liver, and of non-small-cell lung carcinoma.

MET inhibitors are e.g. also may be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrange-ments (e.g. TPR-MET; Cooper et al. Nature 311, 29-33, 1984; Park. et al. Cell 45, 895-904, 1986).

MET inhibitors are e.g. further useful in the treatment of additional cancers and conditions as provided herein or known in the art.

MET inhibitors are e.g. also suitable for the treatment of one or more inflammatory conditions.

In a further embodiment, the inflammatory condition is due to an infection. In one embodiment, the method of treatment would be to block pathogen infection. In a particular embodiment, the infection is a bacterial infection, e.g., a *Listeria* infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF.

The combination product of the present disclosure is especially appropriate for treatment of any of the cancers mentioned above amenable to EGFR or Met inhibitor treatment, especially a cancer selected from adenocarcinoma (especially of the breast or more especially of the lung), rhabdomyosarcoma, osteosarcoma, urinary bladder carcinoma, colorectal cancer and glioma.

The term "a therapeutically effective amount" of a compound of the present disclosure refers to an amount of the compound of the present disclosure that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present disclosure that, when administered to a subject, is effective to (1) at least partially alleviating, inhibiting, preventing and/or ameliorating a condition, or a disorder or a disease (i) mediated by cMet (MET) and/or mediated by EGFR activity, or (ii) characterized by activity (normal or abnormal) of cMet and/or of EGFR; or (2) reducing or inhibiting the activity of cMet and/or of EGFR; or (3) reducing or inhibiting the expression of cMet and/or EGFR. In another non-limiting embodiment, the term "a therapeutically effective amount" refers to the amount of the compound of the present disclosure that, when administered to a cell, or a tissue, or a non-cellular biological material, or a medium, is effective to at least partially reducing or inhibiting the activity of cMet and/or EGFR; or at least partially reducing or inhibiting the expression of MET and/or EGFR.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

"And/or" means that each one or both or all of the components or features of a list are possible variants, especially two or more thereof in an alternative or cumulative way.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "treatment" comprises, for example, the prophylactic or especially therapeutic administration of the combination partners to a warm-blooded animal, preferably to a human being, in need of such treatment with the aim to cure the disease or to have an effect on disease regression or on the delay of progression of a disease.

As used herein, a subject is "in need of" a treatment if such subject would benefit biologically, medically or in quality of life from such treatment.

As used herein, the term "a," "an," "the" and similar terms used in the context of the present disclosure (especially in the context of the claims) are to be construed to cover both the singular and plural unless otherwise indicated herein or clearly contradicted by the context.

The combinations according to the disclosure can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carriers, especially suitable for enteral or parenteral application. In one embodiment of the disclosure, one or more of the active ingredients are administered orally.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical combination product according to the disclosure (as fixed combination, or as kit, e.g. as combination of a fixed combination and individual formulations for one or both combination partners or as kit of individual formulations of the combination partners) comprises the combination partners (at least one MET tyrosine kinase inhibitor, at least one EGFR tyrosine kinase inhibitor, and optionally one or more further co-agents) of the present disclosure and one or more pharmaceutically acceptable carrier materials (carriers, excipients). The combination products or the combination partners constituting it can be formulated for particular routes of administration such as oral administration, parenteral administration, and rectal administration, etc. In addition, the combination products of the present disclosure can be made up in a solid form (including without limitation capsules, tablets, pills, granules, powders or suppositories), or in a liquid form (including without limitation solutions, suspensions or emulsions). The combination products and/or their combination partners can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

In one embodiment, the pharmaceutical compositions are tablets or gelatin capsules comprising the active ingredient together with one or more commonly known carriers, e.g. one or more carriers selected from the group consisting of
  a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration especially include an effective amount of one or more or in case of fixed combination formulations each of the combination partners (active ingredients) in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient(s) in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions (especially useful e.g. where antibodies are used as EGFR inhibitors) are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of one or more active ingredients with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The disclosure relates also to a kit of parts or a fixed pharmaceutical composition comprising an effective amount, especially an amount effective in the treatment of one of the above-mentioned diseases of at least one MET tyrosine kinase inhibitor, at least one EGFR tyrosine kinase inhibitor, or a pharmaceutically acceptable salt thereof, respectively, and optionally of at least one further co-agent, or a pharmaceutically acceptable salt thereof, together with one or more pharmaceutically acceptable carriers that are suitable for topical, enteral, for example oral or rectal, or parenteral administration and that may be inorganic or organic, solid or liquid.

In all formulations, the active ingredient(s) forming part of a combination product according to the present disclosure can be present each in a relative amount of 0.5 to 95% of weight of the corresponding formulation (regarding the formulation as such, that is without packaging and leaflet), e.g. from 1 to 90, 5 to 95, 10 to 98 or 10 to 60 or 40 to 80% by weight, respectively.

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of each of the combination partners or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, e.g. divided preferably into 1 to 3 single doses, e.g. for use once or twice daily, which may, for example, be of the same size. Usually, children receive half of the adult dose.

The pharmaceutical combination product of the present disclosure can e.g. be in unit dosage of about 1-1000 mg of active ingredient(s) for a subject of about 50-70 kg, or about 1-500 mg or about 1-250 mg or about 1-150 mg or about 0.5-100 mg, or about 1-50 mg of for any one or in particular the sum of active ingredients; or (especially for the EGFR inhibitor) 50 to 900, 60 to 850, 75 to 800 or 100 to 600 mg, respectively, for any one or in particular the sum of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or (in animal use) veterinarian of ordinary skill can readily determine the effective amount of each of the active ingredients necessary to prevent, treat or inhibit the progress of the disorder or disease.

Specific embodiments of the disclosure are also given in the claims which are incorporated here by reference, as well as in the Examples.

EXAMPLES

The following Examples illustrate the disclosure and provide specific embodiments, however without limiting the scope of the disclosure.

Example 1 Cell Culture Data

Reagents:

INC280 (NVP-INC280) and Compound A were dissolved in DMSO at 10 mM and stored in aliquots at −20° C.

Cell Culture:

HCC827 was obtained from ATCC. HCC827 GR5 (resistant to Gefitinib) was obtained from Jeff Engleman lab at Massachusetts General Hospital. Both cells were cultured in RPMI-1640 (ATCC, #30-2001) with 10% FBS (Thermo scientific, #SH30071.03) and maintained in a 37° C., 5% CO2 incubator. Cells were passaged twice a week using TrypLE™ Express (Invitrogen, #12604-013), an animal origin-free recombinant enzyme used for dissociating adherent mammalian cells compare to the regular trypsin.

Cell Proliferation Assay:

Cell viability was determined by measuring cellular ATP content using the CellTiter-Glo® (CTG) luminescent cell viability assay (Promega #G7573) according to the manufacturer's protocol. Briefly, cells (3100 for both HCC827 and HCC827 GR5) were seeded in 80 µl growth media per well in clear-bottom 96-well black plates (Costar, #3904) in triplicates. Cells were allowed to attach overnight prior to 72 hours of treatment with indicated compounds (serially-diluted where applicable) for Chalice combination experiment (+20 µl compound A+20 µl compound B). At the end of the drug treatment, 100 ul CTG reagent was added to each well to lyse the cells, and luminescence signals were recorded in the Envision plate reader (Perkin Elmer).

Method for Calculating the Effect of Combinations:

To evaluate the combination effect in a non-bias way and to identify synergistic effect at all possible concentrations, the combination studies were conducted with a "dose matrix", where a combination is tested in all possible permutations of serially-diluted compounds. In all combination assays, compounds were applied simultaneously. This "dose matrix" used in this study is as following: Compound A was subjected to a 7 doses 3× serial dilution with the highest dose at 3 uM and the lowest dose at about 1.37 nM. INC280 was subjected to a 7 doses 3× serial dilution with highest dose at 1.5 uM and lowest dose at about 686 pM. The synergistic interaction was analyzed using Chalice software (CombinatoRx, Cambridge Mass.). Synergy was calculated by comparing a combination's response to those of its single agents, against the drug-with-itself dose-additive reference model. Deviations from dose additives can be assessed numerically with a Combination Index quantify the overall strength of combination effects, which is essentially a volume score $V_{HSA}=\Sigma_{X,Y} \text{Inf}_X \text{Inf}_Y (I_{data}-I_{HSA})$, and it is also calculated between the data and the highest single-agent surface, normalized for single agent dilution factors $f_X, f_Y$ (Lehar et al, 2009).

Figure 2:
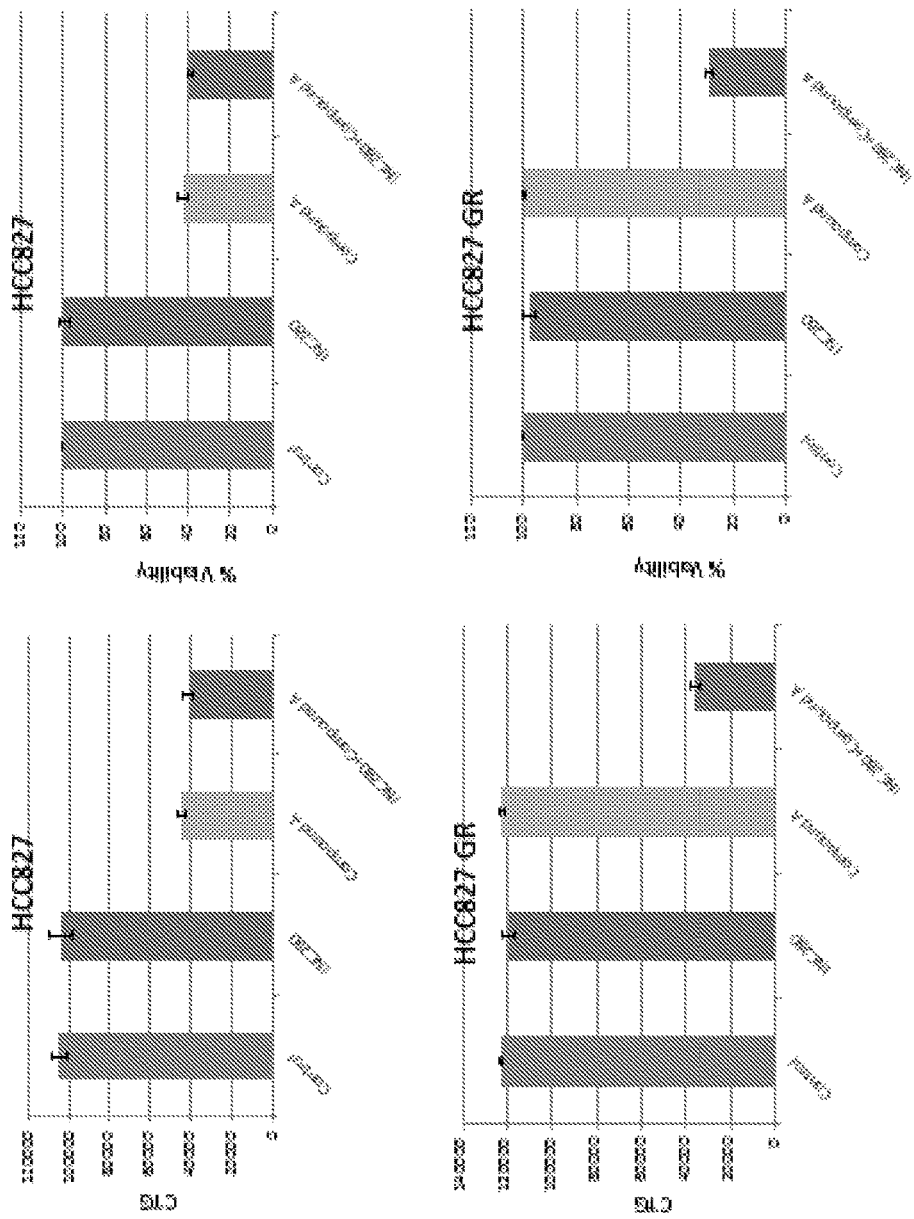
Figure 3:
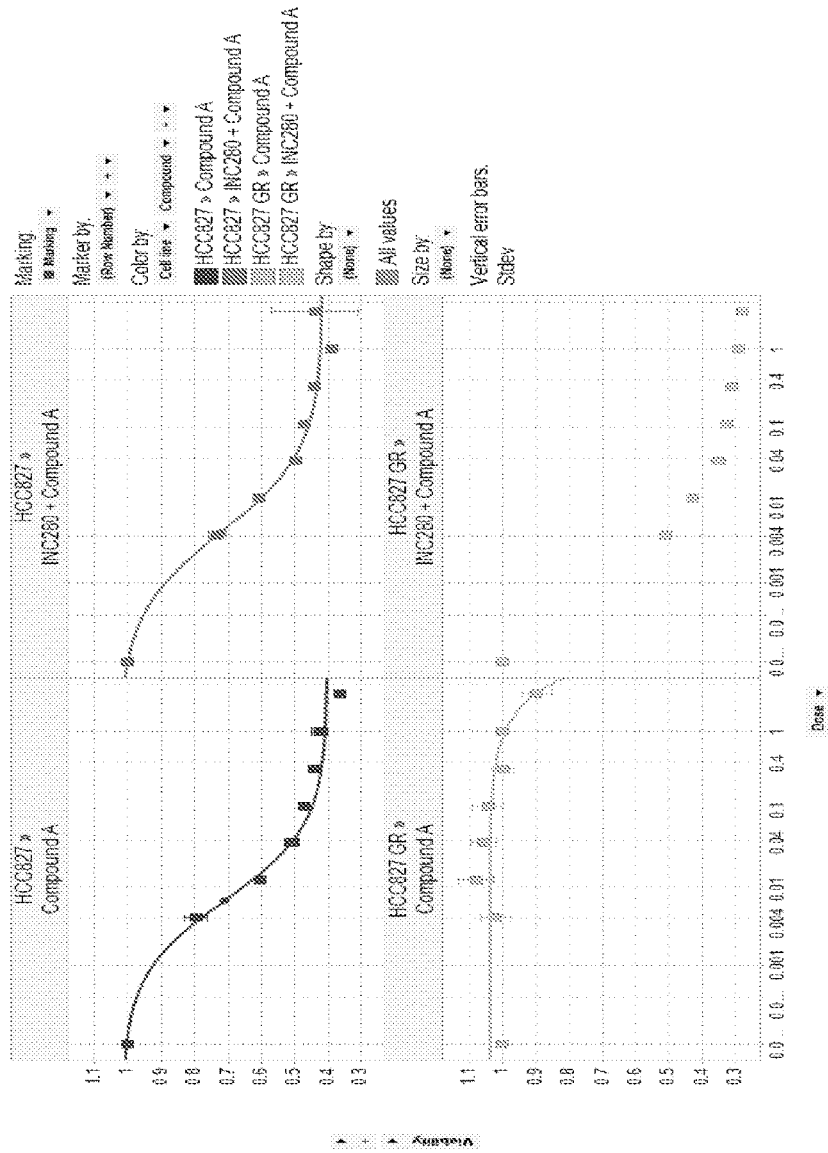
Figure 4:
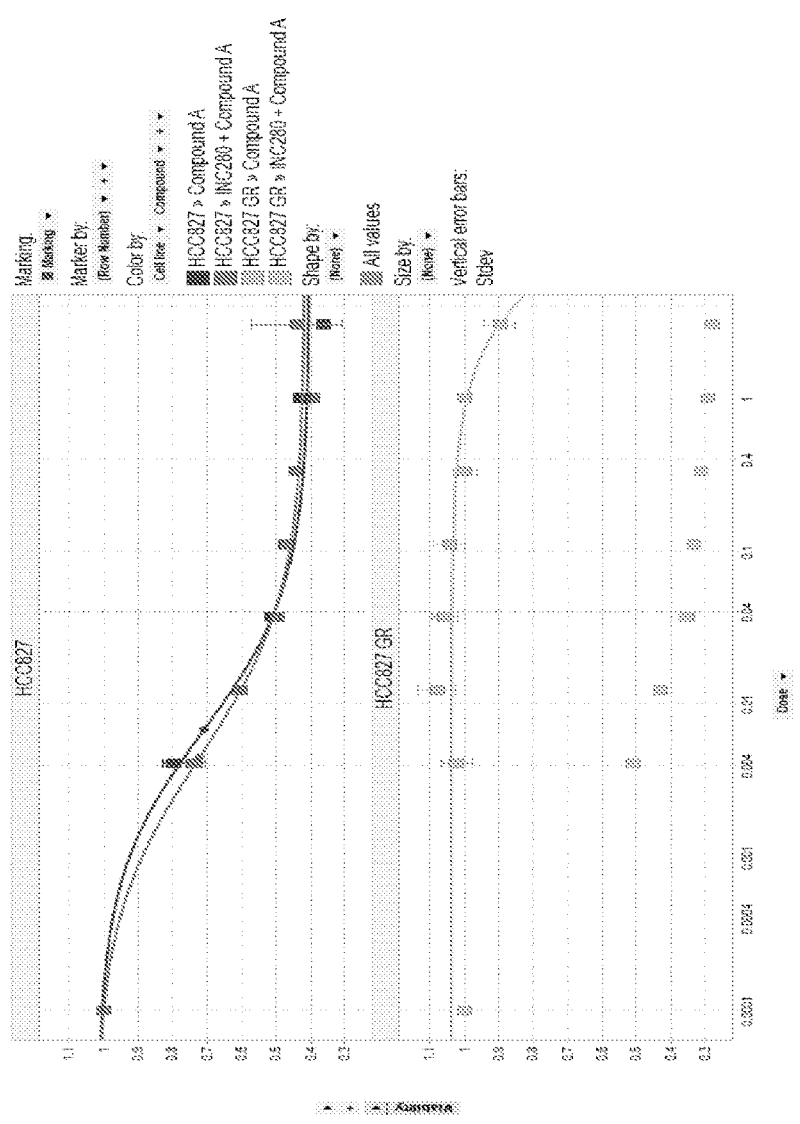

Results:

FIGS. 1-4 demonstrate the results of the combination. Compound A and INC280 benefit each other in HCC-827 Gefitinib resistant line (cMet amplified) while the parental line only respond to Compound A (no combo effect)

Example 2 In Vivo Combination Study Using Compound A and INC280 in Human NSCLC Erlotinib and Compound A Resistant HCC827 Xenograft Model Harboring the Activating EGFR Ex19Del Mutation List of Abbreviations

| Abbreviation | Description |
|---|---|
| ANOVA | Analysis of variance |
| AUC | Area under the curve |
| BIW | Bi-Weekly |
| BLQ | Below limit of quantification |
| BW | Body weight |
| $C_{max}$ | Maximum plasma concentration |
| DLT | Dose limiting toxicity |
| EGFR | Epidermal growth factor receptor |
| EMSI | EGFR mutant selective inhibitor |
| EX19Del | Exon 19 deletion |
| GI | Gastrointestinal |
| hr | Hour |
| HPLC | High Pressure Liquid Chromatography |
| IACUC | Institution Animal Care and Use Committee |
| LC/MS/MS | Liquid Chromatography Tandem Mass Spectrometry |
| LLOQ | Lower limit of quantification |
| MC | Methyl cellulose |
| MTD | Maximal tolerated dose |
| NSCLC | Non-small cell lung cancer |
| PK | Pharmacokinetic |
| PK/PD | Pharmacokinetic/pharmacodynamic |
| p.o. | per os = oral administration |
| QOD | Every other day |
| RPMI-1640 | Roswell Park Memorial Institute Medium |
| TV | Tumor volume |
| % T/C | Percent tumor volume change treated over control group |
| $T_{max}$ | Time to reach $C_{max}$ |
| $T_{1/2}$ | Apparent terminal elimination half-life |
| TCI | Targeted covalent inhibitor |
| TKI | Tyrosine kinase inhibitor |
| TSC | Tumor static concentration |
| QW | Once per week |
| WT | Wild-type |

The in vivo anti-tumor activity of Compound A in combination with INC280 were investigated using Compound A resistant human non-small cell lung cancer (NSCLC) cell line HCC827 as a xenograft subcutaneously implanted in SCID beige mice. NCI-HCC827 harbors the activating and oncogenic Ex19Del EGFR mutation. INC280 is an orally bioavailable, selective c-MET receptor tyrosine kinase inhibitor.

As illustrated in detail below, Compound A in combination with INC280 achieved significant anti-tumor activity in Compound A resistant NSCLC HCC827 tumor bearing SCID beige mice. Daily oral administration of 30 mg/kg Compound A in combination with twice daily oral dose of 10 mg/kg INC280 during course of treatment resulted in significant tumor regressions compared to vehicle control, (p<0.0001). Tumor regression levels achieved in combination were significantly better than either INC280 or Compound A in the monotherapy arms alone, (p<0.0001). Furthermore, Compound A alone was well tolerated with little to no significant body weight loss at the dose tested. INC280 in the monotherapy a BID schedule for this one experiment had a drug holiday on days 7, 8 whereas in the combination arm was not dosed on days 9, 10 and 11. Compound A when dosed in combination with INC280 showed significant tumor regressions in an EGFR resistant setting with a c-MET activation/amplification.

Methods

Test Compounds:
Compound A (in HCl salt form)
Erlotinib (used to condition resistance), and
INC280 (in dihydrochloride salt form)

Formulation:
Compound A (in HCl form) at 30 mg/kg in 0.5% MC (methylcellulose) 0.5% Tween 80, suspension.
Erlotinib at 30-100 mg/kg in 90% water, 10% ethanol/cremophor (1:1), suspension.
INC280-AA-3 (in dihydrochloride salt form) at 10 mg/kg in 0.25% MC (methylcellulose) 0.05% Tween 80 in water, fine suspension.

Materials:
Harlan female Foxn1 nude and SCID beige mice (age 6-8 weeks) were used as the experimental animals. The NCI-HCC827 cell line was purchased from ATCC (American Type Culture Collection, Manassas, Va.). Erlotinib (HCL salt) was purchased from LC Laboratories (Woburn, Mass.) Cat #E-4007 Lot BBE-106. Neutral buffered formalin, Ponceau S Solution #P7170, BSA, TBST, Phosphatase Inhibitor cocktail I and II were purchased from Sigma-Aldrich. Primary Antibody—anti-Phospho-EGF Receptor (Tyr1173) (53A5) (rabbit, 1:1000, Cat #4407, total EGFR (rabbit, 1:1000, Cat #2232) Phospho-Akt (Ser473) (193H12), (rabbit, 1:1000, Cat #4058) and total Akt Rabbit, 1:1000, Cat #9272, Phospho-p44/42 MAPK (Erk1/2) (Thr202/Tyr204) (197G2) Rabbit 1:1000 Cat #4377, Total p44/42 MAPK (Erk1/2) Rabbit 1:1000, Cat #9102, Phospho-MET (Tyr1234/1235) (rabbit-XP mAb, 1:1000, Cell Signaling, Cat #3077) and total MET (rabbit 1:1000, Cell Signaling, Cat #4560) were all purchased from Cell Signaling Technology (Danvers, Mass.). Control Antibody—Rabbit IgG Isotype was purchased from Jackson Immunoresearch (West Grove, Pa.). Super Signal West Pico Chemiluminescent Substrate was purchased from Thermo Scientific, Cat #34087. 3× Complete protease inhibitor tablets were purchased from Roche (Cat. #04693159001). RTK blot were purchased from R&D Systems, Proteome Profiler antibody arrays—Human Phospho-Kinase Array cat. ARY003B and Human Phospho-RTK Array Kit cat. ARY001B.

For all experiments, the animals were housed in a 12 h light/dark cycle facility and had access to food and water ad libitum.

All animal related procedures were conducted under a GNF IACUC approved protocol (P11-308-DD) in compliance with Animal Welfare Act regulations and the Guide for the Care and Use of Laboratory Animals.

Establishment of an Erlotinib/Compound A Resistant NCI-HCC827 Tumor Model

This tumor line was originally established by cell implantation and then consecutive passages, (passage 3) of tumor tissue in SCID beige mice to create a stable tumor line. This stable tumor line was used to create an Erlotinib/Compound A resistant tumor line as described below, FIGS. 5 and 7.

Phospho RTK array shows tumor lysates from HCC827 parental and animal 8 (FIG. 6). Parental HCC827 shows up regulation of pEGFR while pMet is down regulated. The RTK blot in the erlotinib resistant HCC827 shows pEGFR slightly down regulated while pMET is up regulated compared to HCC827 parental.

Erlotinib/Compound A Resistant HCC827 Tumor Stock with cMet Amplification

The donor tumor stocks came from study 11-308-29 mouse #8 for erlotinib and #10, #12 for Compound A resistance for study 11308-138. In study 11-308-29 the naive tumors were dosed with erlotinib starting at 30 mg/kg for 75 days, the dose was increased to 100 mg/kg on day 76 and continued for 32 days. Compound A at 10 mg/kg was dosed for two weeks consecutively and had a drug holiday from days 14 through 30. Compound A dosing was resumed at 10 mg/kg on day 30 through day 60. Compound A was dose escalated to 20 mg/kg from day 60-85 and dose escalated again to 50 mg/kg from day 85 through day 106. When tumors reached 1700 mm$^3$ they were collected. For tissue implantation, mice were anesthetized with continuous flow of 2-4% isoflurane/oxygen mixture using the portable anesthesia induction chamber (Vetequip Inc., Pleasanton, Calif.), 2-3 pieces of the tumor tissue was subcutaneously implanted into 40 SCID beige mice with matrigel (Passage 2) for study 11-308-138 and as described in FIGS. 5 and 7.

The RTK blot in FIG. 8 shows tumor lysates from study 11-308-29 animals 10, 12 (11-308-29 Animal #10 donor source for 11-308-138) pEGFR slightly down regulated and up regulated pMET compared to parental HCC827 previously shown in erlotinib resistance section. Similarly as in erlotinib resistant HCC827 tumors, pEGFR is slightly down regulated and up regulation of pMET as with Compound A resistant HCC827 tumors compared to parental HCC827.

Acute PD Western Blot Using Erlotinib, Compound A, and INC280 as Monotherapies or in Combination in the Resistant NCI-HCC827 Tumors SCID beige mice bearing the Erlotinib resistant tumors (Animals 2-5), n=1 per group, a total of 4 groups and randomized 50 days post tumor fragment implantation with an average tumor volume of 1236.18 mm$^3$ and SD of 316.57 mm$^3$. Compound A resistant HCC827 tumors (Animals 6-16) were randomized into 4 groups (n=3 mice per group) 24 days post tumor fragment implantation with an average tumor volume of 963.24 mm$^3$ with SD 179.56 mm$^3$. Animals in each group received once daily oral administration of Compound A at 30 mg/kg or twice daily INC280-AA-3 at 10 mg/kg alone or in combination.

Pharmacodynamic Measurement

Evaluation of target inhibition of pEGFR and pMET were done by western blot analysis. 40 ∟ gs of tumor lysate proteins were electrophoresed per sample using Criterion 4-12% Bis-Tris gels (Bio-Rad, Cat #345-0124). Upon completion of protein transfer, membranes were incubated with 5% BSA (Sigma) in TBST (25 mM Tris, 150 mM NaCl, 0.1% Tween-20) for 1 h at room temperature to block non-specific binding. Membranes were then incubated with primary antibodies diluted in 5% BSA-TBST against phosphorylated EGFR (EGFR, Y1173) (rabbit, 1:1000, Cell Signaling, Cat #4407, Danvers, Mass.) and total EGFR (rabbit, 1:1000, Cell Signaling, Cat #2232); phosphorylated MET (Y1234/1235), (rabbit-XP mAb, 1:1000, Cell Signaling, Cat #3077) and total MET (rabbit, 1:1000, Cell Signaling Cat #4560) overnight at 4° C. on a rocking platform shaker. After washing 3 times in TBST, 10 minutes each time, the membranes were incubated with secondary antibody HRP-conjugated anti-rabbit (1:2000, Cell Signaling, Cat #7074) in 5% BSA-TBST for 1 h at room temperature. Membranes were then washed 5 times in TBST, 5 minutes each wash, and incubated with Super Signal West Pico Chemiluminescent Substrate (Thermo Scientific Cat #34087) for 2 minutes at room temperature. Chemiluminescent signals were detected by film exposure from 20 sec to 2 min (Thermo CL-XPosure film Cat #34091).

Efficacy Study in an Compound A Resistant HCC827 Mouse Xenograft Model (GNF-11-308-138)

Female SCID beige mice bearing the HCC827 Erlotinib resistant tumors were randomized into 4 groups (n=6 mice per group) 6 days post tumor cell implantation with an average tumor volume range of 89.30-386.24 mm$^3$ (Table 1). Compound A-AA-14 was formulated in 0.5% MC, 0.5% Tween 80 suspension formulation. INC280-AA-3 was formulated in 0.25% MC (methylcellulose) 0.05% Tween 80 in water, solution. Animals in each group received vehicle, Compound A-AA-14 30 mg/kg orally once daily and INC280-AA-3 10 mg/kg orally twice daily at a dosing volume of 5 mL/kg animal body weight during course of treatment. Animals were weighed on dosing days and doses were body weight adjusted. Tumor volumes were measured by digital caliper 3 times a week and body weights of all animals were recorded throughout the study.

Data Analysis

Tumor measurement and body weight:

Body weight was monitored daily and the % change in body weight was calculated as $(BW_{current}-BW_{initial})/(BW_{initial}) \times 100$. Data is presented as percent body weight change from the day of treatment initiation.

Tumor sizes were assessed three times a week once tumors were palpable. Tumor sizes were determined by using caliper measurements. Tumor volumes were calculated with the formula: (Length×Width×Width)/2.

Percent treatment/control (T/C) values for tumor were calculated using the following formula:

$$\% \ T/C = 100 \times \Delta T/\Delta C \text{ if } \Delta T > 0\%$$

$$\% \ Regression = 100 \times \Delta T/T_{initial} \text{ if } \Delta T < 0$$

where:

T=mean tumor volume of the drug-treated group on the final day of the study;

ΔT=mean tumor volume of the drug-treated group on the final day of the study−mean tumor volume of the drug-treated group on initial day of dosing;

$T_{initial}$=mean tumor volume of the drug-treated group on initial day of dosing;

C=mean tumor volume of the control group on the final day of the study; and

ΔC=mean tumor volume of the control group on the final day of the study−mean tumor volume of the control group on initial day of dosing.

All data were expressed as mean±standard error of the mean (SEM). Delta tumor volume and body weight were used for statistical analysis. Between group comparisons were carried out using a one-way ANOVA followed by a post hoc Tukey or Dunn's test. For all statistical evaluations the level of significance was set at p<0.05. Significance compared to the vehicle control group is reported unless otherwise stated.

Results

The anti-tumor activity and tolerability of Compound A and INC280 were examined in EGFRi resistant HCC827 mouse xenograft model. Both erlotinib and Compound A resistant tumor models were established in house. These tumors were confirmed to have c-MET amplification/activation by western and pRTK analysis. A single dose pharmacodynamics (PD) assessment with Compound A, INC280 as monotherapy or in combination suggested that the combination was the most effective in inhibiting both EGFR and cMET phosphorylation. Vehicle and Compound A at a dose of 30 mg/kg, were orally given once daily and INC280 at a dose of 10 mg/kg were orally administered BID by oral gavage for 14 days. However, due to the body weight losses occurring with the INC280 BID schedule a drug holiday was enacted on day 7 and 8 in the monotherapy arm and on days 9, 10 and 11 in the combination arm of the study. Combination of Compound A and INC280 and not either single agent alone lead to tumor regressions in vivo.

Phosphorylation of EGFR and cMet are shown using tumor lysates from parental HCC827 and are either Erlotinib/Compound A resistant tumors (FIG. 3-1) Erlotinib 100 mg/kg, Compound A 30 mg/kg, and INC280 10 mg/kg were all dosed at efficacious levels and tumors were taken at 6 hours post dose.

Efficacy of Compound A in HCC827 Mouse Xenograft:

As shown in FIG. 10, vehicle or Compound A at 30 mg/kg, were dosed orally once daily, and INC280 at 10 mg/kg orally dosed twice daily. Compound A was also evaluated in combination with INC280. The figure shows that Compound A alone was not significantly different from vehicle, (p>0.05) with a T/C of 64%. Compound A alone was significantly different, (p<0.001) with a T/C of 23%. Compound A in combination with INC280 was significantly different from vehicle, (p<0.0001) and induced statistically significant tumor regression (T/C −86%) Furthermore, the combination of Compound A and INC280 was significantly better than either single agents, Compound A or INC280 alone, (p<0.0001). Detailed tumor volume measurements and changes in tumor volume are listed in Appendices Tables 1 and 2.

Tolerability of Compound A in the HCC827 Mouse Xenograft Model

Compound tolerability was monitored by group percent body weight change as shown in FIG. 11. Compound A alone was well tolerated, and body weights were maintained during course of the 14 day treatment. However, INC280 alone had to be given a drug holiday on day 7 and 8 due to body weight change of −8.5% and −5.66% respectively but dosing was resumed on day 9. Because INC280 was also part of the combination group and showed a trend towards body weight loss on day 9, the combination group also received a drug holiday on days 9, 10, and 11 based on group body weight changes of −4.72%, −3.91, and −1.0% and dosing resumed from days 12 through day 14. Initial and final body weight measurements are detailed in Table 3.

Immunohistochemistry Evaluation of pEGFR (400×) and pMET (200×) in the Combination Study IHC and Histology are shown in FIG. 12, Top panel is pEGFR IHC (p-EGFR(D).MS,HU; Histology Immunohistochemistry SOP 33) 100× Bottom panel is pMET IHC (p-Met (D).HU; Histology Immunohistochemistry SOP 53) 100×. From left to right, vehicle, Compound A, INC280, combination Compound A/INC280.

Conclusion and Discussion

Advancement of molecularly targeted therapeutics against EGFR mutations is an important treatment strategy for patients with NSCLC. Of these approximately 5% of EGFR mutation—positive tumors with acquired resistance to EGFR TKIs are found to have MET gene amplification.

Compound A is designed to improve on efficacy of first and second generation EGFR inhibitors while having reduced dose limiting associated toxicities as compared to previous EGFR TKIs. Compound A has the potential to provide an effective therapy for the treatment of NSCLC in combination with INC280 in the patient population that have Met activation/amplification.

Compound A achieved significant anti-tumor activity and tumor regressions in combination with INC280 in HCC827 tumors that are resistant to compound A monotherapy. Following 14 days of once daily oral administration of 30 mg/kg Compound A in combination with 10 mg/kg INC280 dosed BID achieved significant tumor regression (T/C −86%). Compound A alone was well tolerated, with little to no body weight loss observed at 30 mg/kg. INC280 alone showed a slight body weight loss on day 7 at −8.5% and was well tolerated for rest of the study. In combination, even though Compound A and INC280 combination was tolerated a drug holiday was enacted on days 9, 10, and 11 due to the INC280 single agent effects. In conclusion, Compound A in combination with INC280 can provide clinical benefit in patients with NSCLC that are also cMet driven.

TABLE 2

Mean initial and final tumor volume in HCC827 mouse xenograft and anti-tumor effect T/C (percent treated versus control) summary on day 14 following once daily oral dosing of Compound A and or INC280 twice daily oral dosing (study # GNF-11-308-138-Eff-EGFR-Compound A-HCC827)

| Treatment Group | Schedule | Mean initial Tumor Volume (mm³ ± SE) | Mean final Tumor Volume (mm³ ± SE) | Mean T/C |
|---|---|---|---|---|
| Vehicle | BID | 583.69 ± 32.35 | 1339.08 ± 114.21 | 100% |
| Compound A, 30 mg/kg | QD | 578.32 ± 35.84 | 1063.26 ± 93.45 | 64% |
| INC280, 10 mg/kg | BID | 588.17 ± 39.56 | 760.84 ± 81.62 | 23% |

TABLE 1

Individual tumor volume measurement post treatment in HCC827 mouse xenograft (study # GNF-11-308-138-Eff-EGFR-Compound A-INC280 - Compound A resistantHCC827)

| | | Days post implant | | | | | | |
|---|---|---|---|---|---|---|---|---|
| | | 22 | 24 | 27 | 29 | 31 | 34 | 36 |
| | Animal | Days post dosing | | | | | | |
| Treatment | ID | 0 | 2 | 5 | 7 | 9 | 12 | 14 |
| Vehicle 5 ml/kg PO BID | 1 | 489.61 | 529.27 | 730.69 | 875.73 | 919.48 | 1199.86 | 1276.40 |
| | 2 | 492.43 | 605.18 | 659.40 | 716.11 | 855.45 | 798.13 | 855.97 |
| | 3 | 588.55 | 650.18 | 765.33 | 796.25 | 869.55 | 1112.71 | 1277.50 |
| | 4 | 596.75 | 728.48 | 879.93 | 976.38 | 1083.76 | 1291.54 | 1604.06 |
| | 5 | 667.22 | 655.48 | 728.40 | 894.47 | 1118.55 | 1121.67 | 1406.90 |
| | 6 | 667.59 | 826.69 | 1084.73 | 1163.08 | 1124.74 | 1528.88 | 1613.64 |
| | Mean | 583.69 | 665.88 | 808.08 | 903.67 | 995.26 | 1175.46 | 1339.08 |
| | SD | 79.24 | 102.45 | 153.60 | 155.02 | 127.19 | 240.08 | 279.75 |
| Compound A 30 mg/kg QD | 7 | 470.34 | 425.76 | 447.17 | 641.63 | 595.65 | 932.76 | 882.62 |
| | 8 | 502.24 | 474.70 | 509.01 | 591.63 | 822.67 | 885.77 | 1115.99 |
| | 9 | 547.37 | 500.47 | 478.72 | 523.15 | 611.23 | 742.37 | 727.98 |
| | 10 | 597.98 | 718.94 | 709.28 | 792.15 | 877.37 | 1125.55 | 1076.46 |
| | 11 | 657.77 | 679.81 | 723.82 | 837.06 | 891.82 | 1019.63 | 1368.14 |
| | 12 | 694.21 | 723.63 | 730.32 | 800.58 | 940.84 | 1028.22 | 1208.36 |
| | Mean | 578.32 | 587.22 | 599.72 | 697.70 | 789.93 | 955.72 | 1063.26 |
| | SD | 87.79 | 134.75 | 134.61 | 129.45 | 149.37 | 133.51 | 228.91 |
| INC280 10 mg/kg BID | 13 | 456.20 | 531.11 | 869.50 | 690.94 | 646.47 | 688.69 | 1030.71 |
| | 14 | 520.06 | 641.24 | 753.37 | 653.24 | 649.16 | 617.11 | 948.57 |
| | 15 | 543.63 | 502.64 | 556.93 | 589.97 | 572.94 | 487.07 | 521.81 |
| | 16 | 640.13 | 784.24 | 822.50 | 675.03 | 510.69 | 531.80 | 674.65 |
| | 17 | 655.67 | 667.19 | 628.26 | 699.40 | 613.71 | 432.97 | 598.62 |
| | 18 | 713.33 | 674.14 | 834.83 | 627.01 | 594.99 | 585.67 | 790.69 |
| | Mean | 588.17 | 633.43 | 744.23 | 655.93 | 597.99 | 557.22 | 760.84 |
| | SD | 96.91 | 103.13 | 125.41 | 41.65 | 51.91 | 92.40 | 199.92 |
| Compound A/ INC280 | 19 | 410.32 | 417.88 | 191.16 | 114.43 | 82.09 | 71.38 | 59.96 |
| | 20 | 520.77 | 416.99 | 190.72 | 111.16 | 68.66 | 70.17 | 70.32 |
| | 21 | 523.15 | 476.78 | 122.49 | 88.40 | 50.23 | 67.42 | 93.38 |
| | 22 | 644.54 | 569.06 | 319.50 | 190.24 | 95.12 | 62.66 | 80.26 |
| | 23 | 644.88 | 479.18 | 312.85 | 195.90 | 111.63 | 98.37 | 85.01 |
| | 24 | 720.73 | 624.74 | 247.96 | 161.54 | 114.66 | 78.57 | 95.49 |
| | Mean | 577.40 | 497.44 | 230.78 | 143.61 | 87.06 | 74.76 | 80.74 |
| | SD | 112.85 | 83.54 | 77.20 | 45.13 | 25.10 | 12.68 | 13.68 |

Table 1. Human Compound A resistant NSCLC HCC827 tumor fragments were subcutaneously transplanted into the right flank of 6-8 week old female SCID beige mice. Treatment began when an average tumor volume reached ~580 mm³. Vehicle (0.5% MC, 0.5% Tween80) or Compound A at 30 mg/kg was administered once daily and INC280-AA-3 at 10 mg/kg twice daily by oral gavage for 14 consecutive days. Tumor volumes were calculated by caliper measurement, (Length × Width × Width)/2, and were recorded 3 times per week.

TABLE 2-continued

Mean initial and final tumor volume in HCC827 mouse xenograft and anti-tumor effect T/C (percent treated versus control) summary on day 14 following once daily oral dosing of Compound A and or INC280 twice daily oral dosing (study # GNF-11-308-138-Eff-EGFR-Compound A-HCC827)

| Treatment Group | Schedule | Mean initial Tumor Volume (mm³ ± SE) | Mean final Tumor Volume (mm³ ± SE) | Mean T/C |
|---|---|---|---|---|
| Compound A/INC280 | QD/BID | 577.40 ± 46.07 | 80.74 ± 5.59 | −86% |

Human Compound A resistant NSCLC HCC827 tumor fragments were subcutaneously transplanted into the right flank 6-8 week old female SCID beige mice. Treatment began when an average tumor volume reached ~580 mm3. Vehicle (0.5% MC, 0.5% Tween80) or Coumpund A at 30 mg/kg was administered once daily and INC280-AA3 at 10 mg/kg twice daily by oral gavage for 14 consecutive days. Tumor volumes were calculated by caliper measurement, (Length × Width × Width)/2, and were recorded 3 times per week. SE: standard error. Changes in tumor volume for each treated (T) and control (C) group are measured by subtracting the mean tumor volume on the day of first treatment (staging day) from the mean tumor volume on the specified observation day. These values are used to calculate a percent T/C as follows: % T/C = (Δ T/ Δ C) × 100; when Δ T > 0 % T/C = (Δ T/ $T_i$) × 100; when Δ T < 0, $T_i$ is the mean tumor weight at the start of treatment.

TABLE 3

Mean initial and final body weights and percent body weight change on day 14 in mouse Compound A resistant HCC827 xenograft following once daily oral dosing of Compound A or Vehicle and twice daily oral dosing of INC280 (study #11-308-138)

| Treatment Group | Schedule | Initial BW (g) mean ± SD | Final BW (g) mean ± SD | BW (%) mean |
|---|---|---|---|---|
| Vehicle | BID | 20.35 ± 2.82 | 20.22 ± 2.31 | −0.64 |
| Compound A, 30 mg/kg | QD | 21.43 ± 0.77 | 22.58 ± 1.00 | 5.39 |
| INC280, 10 mg/kg | BID | 20.74 ± 0.79 | 19.95 ± 1.58 | −3.83 |
| Compound A/INC280 | QD/BID | 21.53 ± 2.77 | 21.08 ± 2.55 | −2.12 |

Human Compound A resistant NSCLC HCC827 tumor fragments were subcutaneously transplanted into the right flank 6-8 week old female SCID beige mice. Treatment began when an average tumor volume reached ~580 mm3. Vehicle (0.5% MC, 0.5% Tween80) or Coumpund A at 30 mg/kg was administered once daily and INC280 at 10 mg/kg twice daily by oral gavage for 14 consecutive days. Body weights were calculated using mettler balance (grams) and were recorded from day 1 through day 14. SD: standard deviation. The percent change in body weight was calculated as ($BW_{current}$-$BW_{initial}$)/($BW_{initial}$) × 100. Data is presented as percent body weight change from the day of treatment initiation.

Example 3 Compound A in Combination with INC280 in Adult Patients with EGFR Mutated Non-Small Cell Lung Cancer Patients with advanced or metastatic EGFR mutant L858R or ex19del NSCLC can be treated with the combination of Compound A and INC280.

Compound A is administered daily with 50 mg, 75 mg, 150 mg, 300 mg, 450 mg, 600 mg, or 800 mg dose. INC280 is administered 100 mg bid, 200 mg bid, 400 mg bid or 600 mg bid.

The invention claimed is:

1. A pharmaceutical combination comprising
   (i) a MET tyrosine kinase inhibitor which is 2-fluoro-N-methyl-4-[(7-quinolin-6-yl-methyl)-imidazo[1,2-b]triazin-2-yl]benzamide having the formula

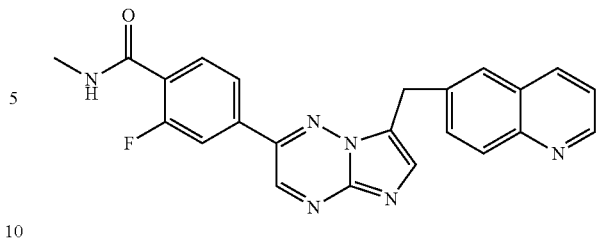

or a pharmaceutically acceptable salt or hydrate thereof,
   (ii) an EGFR tyrosine kinase inhibitor which is (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof.

2. The combination of claim 1, wherein the MET tyrosine kinase inhibitor is in the dihydrochloric acid salt form of 2-fluoro-N-methyl-4-[(7-quinolin-6-yl-methyl)-imidazo[1,2-b]triazin-2-yl]benzamide.

3. The combination of claim 1, wherein the MET tyrosine kinase inhibitor is in the form of a dihydrochloric monohydrate salt of 2-fluoro-N-methyl-4-[(7-quinolin-6-yl-methyl)-imidazo[1,2-b]triazin-2-yl]benzamide.

4. The combination of claim 1, wherein the EGFR tyrosine kinase inhibitor is the hydrochloride salt or the mesylate salt of (R,E)-N-(7-chloro-1-(1-(4-(dimethylamino)but-2-enoyl)azepan-3-yl)-1H-benzo[d]imidazol-2-yl)-2-methylisonicotinamide.

5. The combination of claim 1, further comprising of at least one pharmaceutically acceptable carrier.

6. A method of treating an EGFR tyrosine kinase activity and/or MET tyrosine kinase activity mediated disease, which comprises simultaneous, separate or sequential administration to a subject in need of such treatment,
   (i) a MET tyrosine kinase inhibitor which is 2-fluoro-N-methyl-4-[(7-quinolin-6-yl-methyl)-imidazo[1,2-b]triazin-2-yl]benzamide having the formula

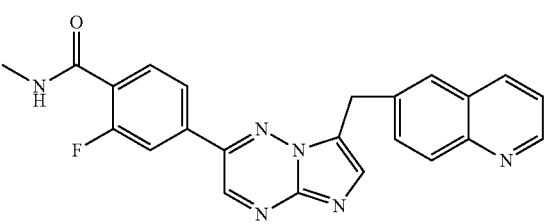 [SMILES: CNC(=O)c1ccc(-c2cnc3ncc(Cc4ccc5ncccc5c4)n3n2)cc1F]

or a pharmaceutically acceptable salt or hydrate thereof, and
   (ii) an EGFR tyrosine kinase inhibitor which is (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof, wherein treatment refers to ameliorating the disease or disorder, alleviating or ameliorating at least one physical parameter including those which may not be discernible by the patient, or modulating the disease or disorder, either physically, physiologically, or both.

7. The method of claim 6 wherein the EGFR tyrosine kinase activity and/or MET tyrosine kinase activity mediated disease is cancer.

8. The method of claim 7, wherein the cancer is a carcinoma, a musculoskeletal sarcoma, a soft tissue sarcoma, a hematopoietic malignancy, or another neoplasm.

9. The method of claim 7, wherein the cancer is an EGFR resistant tumor with a c-MET activation/amplification.

10. The method of claim 7, wherein the cancer is non-small cell lung cancer (NSCLC).

11. The method of claim 7, wherein the cancer is metastatic non-small cell lung cancer.

12. The method of claim 7, wherein the cancer is resistant to treatment with erlotinib, gefitinib or afatinib.

13. The method of claim 7, wherein the cancer is resistant to treatment with (R,E)-N-(7-chloro-1-(1-(4-(dimethylamino)but-2-enoyl)azepan-3-yl)-1H-benzo[d]imidazol-2-yl)-2-methylisonicotinamide as monotherapy.

14. The method of claim 7, wherein the cancer is colorectal cancer (CRC) or metastatic colorectal cancer (mCRC).

15. The method of claim 7, wherein the cancer is head and neck cancer or metastatic head and neck cancer or head and neck squamous cell carcinoma (HNSCC).

16. The method of claim 8, wherein the carcinoma is bladder, breast, cervical, cholangiocarcinoma, colorectal, esophageal, gastric, head and neck, kidney, liver, lung, nasopharygeal, ovarian, pancreas, prostate, or thyroid carcinoma.

17. The method of claim 8, wherein the musculoskeletal sarcoma is osteosarcaoma, synovial sarcoma, or rhabdomyosarcoma.

18. The method of claim 8, wherein the soft tissue sarcoma is MFH/fibrosarcoma, leiomyosarcoma, or Kaposi's sarcoma.

19. The method of claim 8, wherein the hematopoietic malignancy is multiple myeloma, lymphomas, adult T cell leukemia, acute myelogenous leukemia, or chronic myeloid leukemia.

20. The method of claim 8, wherein the another neoplasm is glioblastomas, astrocytomas, melanoma, mesothelioma or Wilm's tumor.

21. The method of claim 7, wherein the cancer is EGFR mutated non-small cell lung cancer.

22. The method of claim 7, wherein the cancer is EGFR mutant L858R non-small cell lung cancer.

23. The method of claim 7, wherein the cancer is EGFR mutant ex19del non-small cell lung cancer.

24. The method of claim 6, wherein 2-fluoro-N-methyl-4-[(7-quinolin-6-yl-methyl)-imidazo[1,2-b]triazin-2-yl]benzamide or a pharmaceutically acceptable salt and (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof are administered simultaneously.

25. The method of claim 6, wherein 2-fluoro-N-methyl-4-[(7-quinolin-6-yl-methyl)-imidazo[1,2-b]triazin-2-yl]benzamide or a pharmaceutically acceptable salt and (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof are administered separately.

26. The method of claim 6, wherein 2-fluoro-N-methyl-4-[(7-quinolin-6-yl-methyl)-imidazo[1,2-b]triazin-2-yl]benzamide or a pharmaceutically acceptable salt and (R,E)-N-(7-chloro-1-(1-(4-(dimethylamino)but-2-enoyl)azepan-3-yl)-1H-benzo[d]imidazol-2-yl)-2-methylisonicotinamide, or a pharmaceutically acceptable salt thereof are administered sequentially.

* * * * *